(12) United States Patent
Fu et al.

(10) Patent No.: US 10,779,988 B2
(45) Date of Patent: Sep. 22, 2020

(54) COMPACT ULTRA-SHORT PULSED LASER EYE SURGERY WORKSTATION

(71) Applicant: AMO Development, LLC, Santa Ana, CA (US)

(72) Inventors: Hong Fu, Pleasanton, CA (US); Bryant M. Moore, Pittsboro, NC (US); Charles Vice, San Juan Capistrano, CA (US)

(73) Assignee: AMO Development, LLC, Santa Ana, CA (US)

( * ) Notice: Subject to any disclaimer, the term of this patent is extended or adjusted under 35 U.S.C. 154(b) by 1286 days.

(21) Appl. No.: 14/970,898

(22) Filed: Dec. 16, 2015

(65) Prior Publication Data

US 2016/0374857 A1 Dec. 29, 2016

Related U.S. Application Data

(60) Provisional application No. 62/183,637, filed on Jun. 23, 2015.

(51) Int. Cl.
*A61F 9/008* (2006.01)
*A61F 9/009* (2006.01)

(52) U.S. Cl.
CPC .......... *A61F 9/00814* (2013.01); *A61F 9/009* (2013.01); *A61F 9/0084* (2013.01);
(Continued)

(58) Field of Classification Search
CPC .. A61F 9/008; A61F 9/00804; A61F 9/00814; A61F 9/0084; A61F 2009/00897
(Continued)

(56) References Cited

U.S. PATENT DOCUMENTS 4,848,340 A * 7/1989 Bille .................. A61B 3/113
606/4
8,171,937 B2 5/2012 Bendett et al.
(Continued)

FOREIGN PATENT DOCUMENTS

| EP | 1475033 A1 | 11/2004 |
|---|---|---|
| WO | 2011091283 A1 | 7/2011 |
| WO | 2013053367 A1 | 4/2013 |

OTHER PUBLICATIONS

Squier J., et al., "Phase and Amplitude Control for Compact, High-Intensity Femtodecond Lasers," Lasers and Electro-Optics Society Annual Meeting, 1996, vol. 1,pp. 52-53.
(Continued)

*Primary Examiner* — John R Downey
(74) *Attorney, Agent, or Firm* — Johnson & Johnson Surgical Vision, Inc.

(57) ABSTRACT

A compact system for performing laser ophthalmic surgery is disclosed. An embodiment of the system includes a mode-locked fiber oscillator-based ultra-short pulsed laser capable of producing laser pulses in the range of 1 nJ to 5 µJ at a pulse repetition rate of between 5 MHz and 25 MHz, a resonant optical scanner oscillating at a frequency of 200 Hz and 21000 Hz, a scan-line rotator, a movable XY-scan device, a z-scan device, and a controller configured to coordinate with the other components of the system to produce one or more desired incision patterns. The system also includes compact visualization optics for in-process monitoring using a beam-splitter inside the cone of a patient interface used to fixate the patient's eye during surgery. The system can be configured such that eye surgery is performed while the patient is either sitting upright, or lying on his or her back.

28 Claims, 26 Drawing Sheets

(52) U.S. Cl.
CPC ............... *A61F 2009/0087* (2013.01); *A61F 2009/00872* (2013.01); *A61F 2009/00897* (2013.01)

(58) Field of Classification Search
USPC .......................................................... 606/4–6
See application file for complete search history.

(56) References Cited

U.S. PATENT DOCUMENTS

| | | |
|---|---|---|
| 8,194,709 B2 | 6/2012 | Kaertner et al. |
| 8,416,817 B2 | 4/2013 | Chong et al. |
| 2005/0228366 A1* | 10/2005 | Kessler ................. A61F 9/0084 606/5 |
| 2007/0050165 A1* | 3/2007 | Gray ........................ A61B 3/00 702/108 |
| 2007/0173794 A1* | 7/2007 | Frey ........................ A61F 9/008 606/5 |
| 2007/0252951 A1* | 11/2007 | Hammer ................. A61F 9/008 351/221 |
| 2008/0077121 A1* | 3/2008 | Rathjen ................... A61F 9/008 606/5 |
| 2008/0243107 A1 | 10/2008 | Muhlhoff et al. |
| 2009/0247999 A1 | 10/2009 | Tuan et al. |
| 2011/0028958 A1 | 2/2011 | Raksi et al. |
| 2011/0118713 A1* | 5/2011 | Raksi ................... A61F 9/00825 606/6 |
| 2011/0206070 A1 | 8/2011 | Karavitis |
| 2011/0206071 A1* | 8/2011 | Karavitis .............. A61F 9/0084 372/25 |
| 2012/0029491 A1 | 2/2012 | Rathjen |
| 2012/0165798 A1 | 6/2012 | Rathjen |
| 2013/0158392 A1* | 6/2013 | Papac ..................... A61F 9/008 600/425 |
| 2013/0335703 A1* | 12/2013 | Creasey ................ A61B 3/0008 351/206 |
| 2014/0058367 A1* | 2/2014 | Dantus .................... H01S 3/005 606/6 |
| 2014/0128856 A1* | 5/2014 | Wysopal ............. A61F 9/00825 606/5 |
| 2014/0180265 A1* | 6/2014 | Huang ................ A61F 9/00827 606/5 |
| 2014/0222050 A1 | 8/2014 | Heitel |
| 2014/0228825 A1* | 8/2014 | Gorschboth ............ A61F 9/008 606/5 |

OTHER PUBLICATIONS

Partial International Search Report for Application No. PCT/US2015/065989, dated Apr. 22, 2016, 6 pages.
International Search Report and Written Opinion for Application No. PCT/US2015/065989, dated Aug. 1, 2016, 18 pages.

* cited by examiner

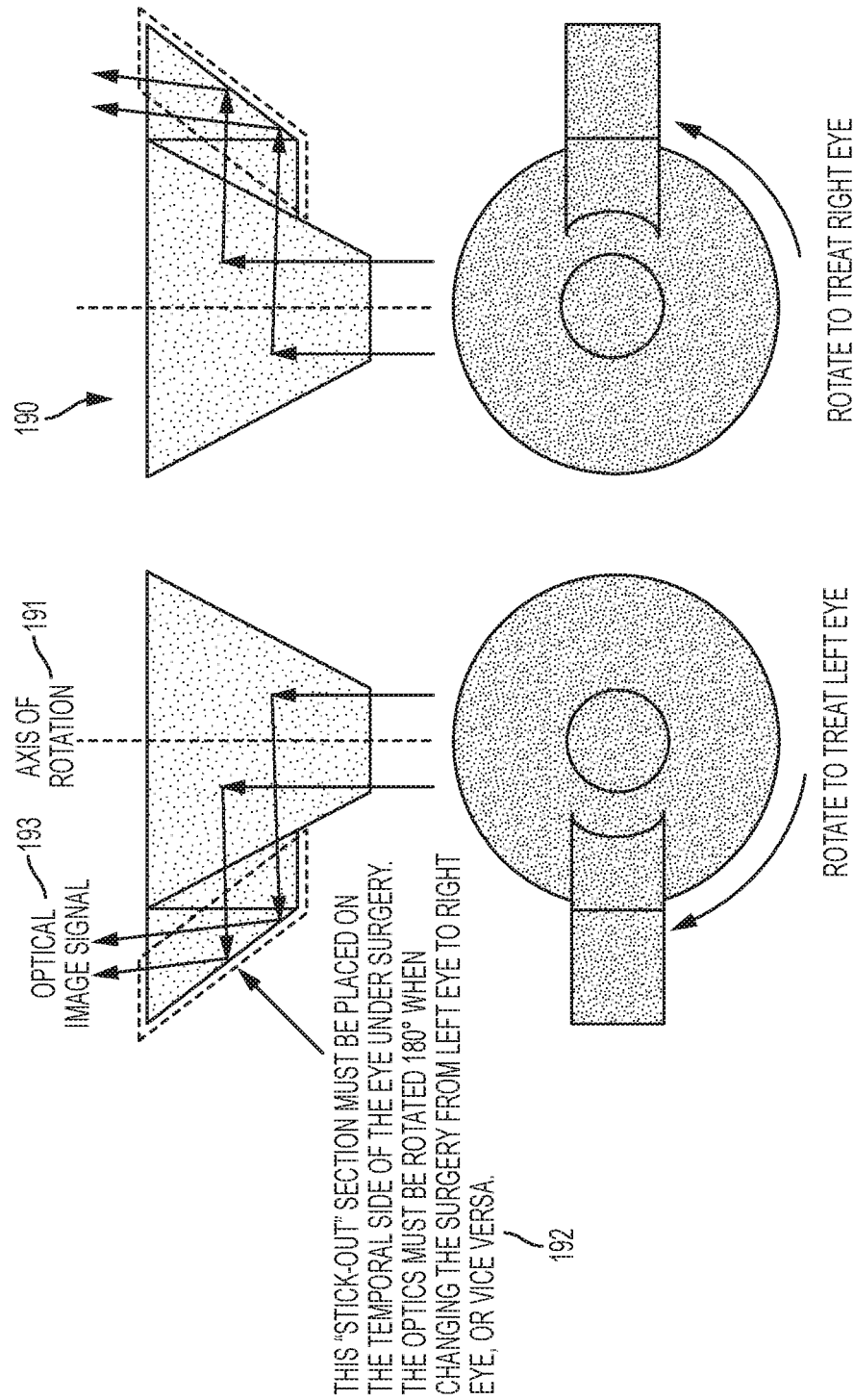

220

Calculate Visualization Beam Exit Heights

|    | Parameter | Symbol | Formula | Value | Unit |
|----|-----------|--------|---------|-------|------|
| 1  | Numerical Aperture | NA | Input | 0.600 | Dimensionless |
| 2  | Refractive Index | n | Input | 1.500 | Dimensionless |
| 3  | Cone Angle | α | α = arcsin(NA/n) | 23.578 | degree |
| 4  | Beam Splitting Surface Angle | β | Input | 24.000 | degree |
| 5  | Glass Height (Disposable+Spacer) | h1 | Input | 8.200 | mm |
| 6  | Radius of Field View | R | Input | 5.500 | mm |
|    | Calculate Edge Ray Exit Height | | | | |
| 7  | Edge Ray Deviation Angle | γ | Input | 7.500 | degree |
| 8  | Auxiliary | AB | AB=h1/cos(α) | 8.947 | mm |
| 9  | Auxiliary | Angle AEB | Angle AEB=90-β-γ | 58.500 | degree |
| 10 | Auxiliary | BE | BE=AB*sin(α+γ)/sin(AEB) | 5.417 | mm |
| 11 | Edge Ray Exit Angle | θ2 | θ2 = 90-2β-γ | 34.500 | degree |
| 12 | Auxiliary | Angle BEF | Angle BEF = 90+β+γ | 121.500 | degree |
| 13 | Auxiliary | BF | BF=BE*sin(BEF)/sin(θ2) | 8.154 | mm |
| 14 | Auxiliary | BP | BP=2*R+2*h1*tan(α) | 18.156 | mm |
| 15 | Auxiliary | FP | FP=BP-BF | 10.004 | mm |
| 16 | Auxiliary | Angle FKP | Angle FKP=2β+γ-α | 31.922 | degree |
| 17 | Auxiliary | FK | FK=FP*sin(90+α)/sin(FKP) | 17.339 | mm |
| 18 | Height of Exit Point for Edge Ray | h3 | h3=FK*sin(θ2) | 9.821 | mm |
|    | Calculate Center Ray Exit Height | | | | |
| 19 | Auxiliary | BQ | BQ=BP/2 | 9.078 | mm |
| 20 | Auxiliary | GQ | GQ=BQ*tan(β) | 4.042 | mm |
| 21 | Center Ray Exit Angle | θ4 | θ4=90-2β | 42.000 | degree |
| 22 | Auxiliary | HQ | HQ=GQ/tan(θ4) | 4.489 | mm |
| 23 | Auxiliary | HP | HP=PQ-HQ | 4.590 | mm |
| 24 | Auxiliary | Angle HJP | Angle HJP=2β-α | 24.422 | degree |
| 25 | Auxiliary | HJ | HJ=HP*sin(90+α)/sin(HJP) | 10.174 | mm |
| 26 | Height of Exit Point for Center Ray | h2 | h2=HJ*sin(90-2β) | 6.808 | mm |
|    | Calculate Beam Splitter Height | | | | |
| 27 | Auxiliary | Angle BSP | Angle BSP=90-α-β | 42.422 | degree |
| 28 | Auxiliary | BS | BS=BP*sin(90+α)/sin(BSP) | 24.670 | mm |
| 29 | Height of Beam Splitter | h4 | h4=BS*sin(β) | 10.034 | mm |

Figure 19

COMPACT ULTRA-SHORT PULSED LASER EYE SURGERY WORKSTATION

CROSS-REFERENCE TO RELATED APPLICATIONS

This application is a non-provisional application and claims the benefit under 35 U.S.C. § 119(e) of U.S. Provisional Application Ser. No. 62/183,637, filed Jun. 23, 2015, which is incorporated herein in its entirety by reference.

TECHNICAL FIELD

Embodiments of this invention generally relate to the field of eye surgery, and more specifically to ophthalmic laser surgery using a mobile, compact surgical system having a mode-locked fiber oscillator-based ultra-short pulsed laser, a resonant optical scanner, a scan-line rotator, a movable XY-scanning stage, a z-scan mechanism, a controller, and compact visualization optics. The system can be configured such that eye surgery can be performed while the patient is in supine position. Alternatively, the system may be configured so that surgery is performed while the patient is sitting up in an upright position.

BACKGROUND

Vision impairments such as myopia (near sightedness), hyperopia (far sightedness), and astigmatism can be corrected using eyeglasses or contact lenses. Alternatively, they can be corrected with eye surgery.

Traditionally, surgeons performed eye surgery using manual surgical tools, such as microkeratomes and forceps. More recently, however, laser ophthalmic surgery has gained popularity. Surgical laser systems are now used in a variety of ways to treat visual disorders such as myopia, hyperopia, astigmatism, cataracts, and glaucoma. Physicians prefer a surgical laser beam over manual tools because it can be focused accurately on extremely small amounts of ocular tissue, thereby enhancing precision and reliability of the procedure, as well as improving healing time. Studies show that more patients achieve an improved level of post-operative visual acuity in the months after surgery with a laser system than with manual tools.

Depending on the procedure, and/or the required visual correction or indication, laser eye surgery may involve one or more types of surgical lasers, including for example, ultraviolet excimer lasers, and near-infrared, ultra-short pulsed lasers that emit radiation in the picosecond or femtosecond range. Non-ultraviolet, ultra-short pulsed lasers emit radiation with pulse durations as short as 10 femtoseconds and as long as 3 nanoseconds, and with a wavelength between 300 nm and 3000 nm. Both ultraviolet and non-ultraviolet ultra-short pulsed lasers are used in the commonly-known LASIK (laser in-situ keratomileusis) procedure.

With LASIK, a surgeon typically uses a non-ultraviolet, ultra-short pulsed laser to cut a superficial flap in the cornea, which is still attached to epithelial tissue in a hinged area. The surgeon lifts the flap to expose the corneal stroma, which he or she then photoablates with an ultraviolet excimer laser to reshape the cornea. Reshaping the cornea helps correct refractive vision problems such as myopia, hyperopia, and astigmatism.

Besides cutting cortical flaps, non-ultraviolet, ultra-short pulsed lasers are used for other types of eye surgery, including for example, performing incisions for corneal implants, performing intrastromal incisions for refractive correction including astigmatism, as well as performing incisions for cataract surgery, such as clear conical incisions that allow access to the lens capsule, capsulotomy that incises the capsular bag for access to the cataractous lens, and incisions in the lens for softening and segmenting the lens so it can be removed from the eye, and replaced with an artificial intraocular lens.

Conventional ultra-short pulsed laser systems are typically large, bulky, and complex, requiring significant storage space and cumbersome maintenance. For example, Abbott Medical Optics Inc.'s iFS Advanced Femtosecond Laser System is a fixed system of approximately 47"W×41"L×60"H with a weight of 865 lbs. Alcon's Wavelight FS200 System weighs about 970 lbs with a standard bed, and approximately 1050 lbs with a swiveling bed. Its dimensions are approximately 98"W×59"L×51"H for a laser with a standard bed, and 98"W×86"L×51"H for a laser with a swiveling bed. Carl Zeiss Meditec AG's VisuMax Laser System is about 150"×173" big and weighs about 1916 lbs. Indeed, Ziemer's LDV Z4, Z6, and Z8 systems, which are the smallest available systems on the market are about 22"W×40"L×30"H, and weigh about 473 lbs. As would be expected, these systems require large room for storage. For instance, the iFS Advanced Femtosecond Laser System requires approximately 3.5×4.2 m² storage space.

Moreover, because these conventional laser machines are large and contain complex optics, they often require a mechanical arm such as an articulating arm or a gantry to support the optical head. The systems also require cooling mechanisms for the laser generator. The complexity of the opto-mechanical design is further exacerbated due to safety and accuracy requirements for the mechanical arm configuration. And, their large footprint and complexity in turn makes these conventional ultra-short pulsed laser systems costly to manufacture as well as to maintain.

Since a corneal flap is prepared before treatment with an excimer laser during LARK, surgeons find it convenient to place the non-ultraviolet ultra-short pulsed laser near an excimer system so as to improve the workflow as well as to enhance sterility and reduce the potential for infection. But, sometimes, the mere size of the systems requires that the flap-cutting laser be located outside the operating room in a different area from the excimer laser system. Most of these laser systems are fixed systems, however, so moving them from room-to-room is not a feasible option. Further, moving the system from room-to-room may not be preferred because the systems have complex and sensitive optical components. Having the systems located in different rooms impacts workflow.

Hence, there is a need for improved utra-short pulsed laser surgery systems that can perform robustly while serving larger patient populations and providing better workflow to physicians.

SUMMARY OF THE INVENTION

Accordingly, this disclosure provides systems and methods for use in suitable ophthalmic laser surgery systems so as to obviate one or more problems due to limitations and disadvantages of the related art. Embodiments as described herein provide improved methods and apparatus to facilitate ophthalmic surgical procedures for the eye.

In a first aspect, an ophthalmic surgical laser system includes a laser delivery system configured to deliver a pulsed laser beam at a focal point of a target in a patient's eye, the pulsed laser beam having a pulse repetition rate in the range between 5 MHz and 25 MHz. A resonant optical scanner is provided with the scanner oscillating at a frequency between 200 Hz and 21000 Hz. An xy-scan device is configured to move the pulsed laser beam in a lateral direction. A z-scan device is configured to modify a depth of focus of the pulsed laser beam. A controller is operably coupled with the laser delivery system, the xy-scan device and the z-scan device. The controller is configured to direct the laser delivery system to output the pulsed laser beam in a desired pattern at the focal point of the target in the eye so as to modify the target.

In some embodiments, the laser delivery system may include a diode-pumped fiber laser. The diode-pumped fiber laser may include a mode-locked fiber oscillator-based laser. The mode-locked fiber oscillator-based laser may be a single-mode, double-clad fiber oscillator. The laser delivery system may further be a fiber laser amplifier. The mode-locked fiber oscillator-based laser may further include all positive dispersion elements.

In some embodiments, the laser delivery system may deliver the pulsed laser beam at the focal point of the target in a patient's eye in a raster pattern. The focal point of the target in the patient's eye may include one or more of a cornea, stroma, capsular bag, crystalline lens, and zonule.

In some embodiments, the laser delivery system may produce the pulsed laser beam having a pulse duration between the range of 10 femtoseconds and 10 picoseconds. The laser delivery system may be configured to produce the pulsed laser beam having a pulse energy between the range of 1 nJ and 5 µJ. The laser delivery system may be configured to produce the pulsed laser beam having a wavelength between the range of 1020 nm and 1060 nm. The laser delivery system may further include a closed-loop control mechanism.

In some embodiments, the resonant optical scanner may be configured to scan the pulsed laser beam from the laser delivery system in a line. The laser system may further include a scan-line rotator, the scan-line rotator may be configured to rotate the scanned line in a desired orientation.

In some embodiments, the xy scan device may be a movable xy scanning stage having a final focusing objective mounted thereon. The movable xy-scanning stage may be a recoilless stage configured to reduce or eliminate mechanical vibration. The xy-scanning stage may be configured to move the pulsed laser beam in a lateral direction such that the laser beam covers the entire surgical field of the patient's eye.

In some embodiments, the pulsed laser beam modifies the target in the patient's eye to produce corneal tissue modification. The corneal tissue modification may include corneal cross-linking.

In some embodiments, the pulsed laser beam modifies the target in the patient's eye to produce a desired incision. The desired incision includes one or more of an xy lamellar dissection, a spiral lamellar dissection, a vertical side-cut, a plano-vertical side cut, an intrastromal incision, a lenticular incision, and any three-dimensional dissection.

In some embodiments, the ophthalmic surgical laser system may include an imaging video camera. The z-scan device may be a fast-z scan device. The ophthalmic surgical laser system may include a beam expander. An interface may be provided for coupling the patient's eye to the ophthalmic surgical laser system. An auto-z module may be configured to measure a distal end of a lens cone of the patient interface coupled to the patient's eye and to provide a depth reference for the z-scan device of the ophthalmic laser system.

In some embodiments, the laser delivery system delivers the pulsed laser beam to the focal point of the target in the patient's eye while the patient is seated in an upright position or in a reclining position.

In another embodiment, an interface is provided for coupling a patient's eye to an ophthalmic surgical laser system. The interface includes a lens cone defining a first plane surface coupled with a delivery tip of the ophthalmic laser system. The lens cone further includes an apex ring coupled to the first plane surface, the apex ring comprising a distal end. A first receptacle is configured to receive an attachment ring, the attachment ring configured to overlay an anterior surface of the patient's eye. A central cavity is configured to receive the lens cone.

In some embodiments, the first receptacle and the attachment ring are disposable. The interface includes a contact lens configured to applanate the anterior surface of the patient's eye.

In some embodiments, one or more beam-splitter optics are configured to allow a pulsed laser beam to pass through the interface to a focal point of the target in the patient's eye. The beam-splitter optics may include one or more multi-facet beam-splitter optics. The beam-splitter optics may include a side-imaging optical channel that is configured to rotate to a temporal side of the patient's eye. The beam-splitter optics may include dual imaging channels. The beam-splitter optics may be configured to manipulate non-telecentric imaging rays at a full optical cone angle equal to or greater than fifteen degrees.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 17 illustrates a patient interface according to an embodiment of the present invention.

FIG. 19 illustrates a table of visualization parameters according to an embodiment of the present invention.

DETAILED DESCRIPTION OF THE EMBODIMENTS

Embodiments of this invention are generally directed to systems and methods for laser-assisted ophthalmic procedures.

Figure 1A:
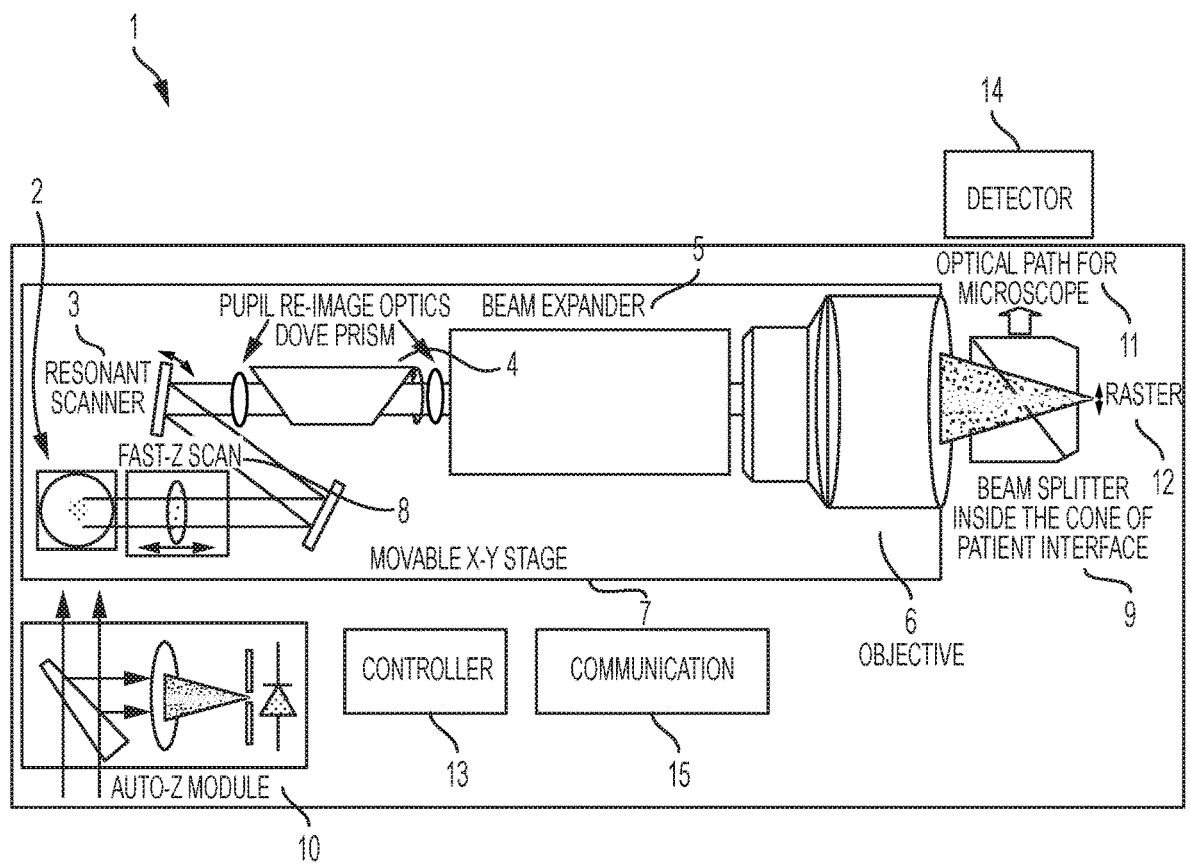
FIGS. 1A and 1B are simplified diagram views of a surgical ophthalmic laser system according to an embodiment of the present invention.

Referring to the drawings, FIG. 1A shows an ophthalmic surgical laser system 1 for making an incision in a target material such as a cornea of an eye. A laser 2 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. The laser may be a micro-chip picosecond laser. For example, a laser beam delivery system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

Although the laser system 1 may be used to photoalter a variety of materials (e.g., organic, inorganic, or a combination thereof), the laser system 1 is suitable for ophthalmic applications. For example, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue.

The system 1 includes, but is not limited to, a laser source 2 capable of generating a pulsed laser beam, a resonant scanner 3 for producing a fast scan line or raster 12 of the pulsed laser beam, an XY scan device 4 or scan line rotator (e.g., a Dove prism, Pechan prism, or the like) for rotating the scan line 12, a beam expander 5, an objective 6, a moveable XY stage 7 for deflecting or directing the pulsed laser beam from the laser 1 on or within the target, a fast-Z scan device 8, a patient interface 9 that may include a visualization beam splitter inside a cone, an auto-Z device 10 for modifying the depth of the pulse laser beam and providing a depth reference, an optical path 11, a controller 13, and a communication module 15. An imaging video camera may further be included.

The laser beam delivery system of the system 1 delivers a pulsed laser beam at a focal point of a target in a patient's eye in a raster pattern and may include the resonant scanner 3, beam expander 5, objective 6 and patient interface 9.

The focal point of the target in the patient's eye may include one or more of a cornea, stroma, capsular bag, crystalline lens, and zonule. The pulsed laser beam may modify the target in the patient's eye to produce corneal tissue modification such as corneal cross-linking. As a result of the pulsed laser beam, a desired incision may be produced in the patient's eye.

The resonant scanner 3 generates a fast scan line at a fixed resonant frequency. The resonant scanner 3 may produce a raster between 1 mm and 2 mm where a width of the scan line may be adjusted. A resonant scanner scans very fast and produces a one-dimensional scan that is, for example, a horizontal line.

The XY scan device 4 or scan line rotator moves the pulsed laser beam raster 12 in a lateral direction so as to rotate the scan line to any desired orientation on an XY plane. For example, a Dove prism or Pechan prism rotates the raster to any direction on an XY plane such as a scan line perpendicular to the XY device 7 trajectory to provide scan coverage over a larger area.

The XY scan device 7 is a movable XY scanning stage having a final focusing objective 6 mounted thereon. The XY scan device 7 carries the final objective 6 to move the fast scan line to cover an entire treatment area. The movable XY scanning stage 7 may include a recoilless stage configured to reduce or eliminate mechanical vibration. The XY scanning stage 7 is configured to move the pulsed laser beam in a lateral direction such that the laser beam may cover an entire surgical field of the patient's eye. Accordingly, the scan line rotator 4 modifies an orientation of the scan line while the moveable XY scanning stage moves the optical field of the scan line across an XY plane.

The fast Z scan device 8 modifies a depth of focus of the pulsed laser beam and may provide fine depth control. The fast Z scan device 8 may either be set at a fixed position or run dynamically to correct the system's inherent depth variations at different (X,Y) locations. In the latter case, a fast Z position is determined by the XY trajectory and does not affect the XY trajectory. A fast Z scan sets a cut depth and moves the focus in the depth direction to produce, for example, a side-cut in a target material.

A shutter (not shown) can be kept open during a bed cut or may be controlled to open/close to block the unwanted pulses during a bed cut.

The patient interface 9 couples the patient's eye to the ophthalmic surgical laser system 1. The patient interface design has a fixed cone nose on the system. The disposable part of the patient interface is single-piece device that allows the use of flat applanation, or the use of liquid interface, for patient sitting upright, respectively. Any design with a separated suction ring does not apply for a patient sitting upright. The patient interface 9 may include a visualization beam splitter in the cone of the patient interface. A beam splitter is placed inside this cone to allow the full eye to be imaged via visualization optics. This allows the system to be made smaller. The patient interface may be removed when an eye-tracking system is used. Visualization may be provided through, for example, a video microscope or ocular microscope.

The auto Z module 10 measures a distal end surface of a lens cone of the patient interface coupled to the patient's eye and provides a depth reference for the Z scan device 8 of the ophthalmic laser system. The auto Z module 10 uses the focus of a surgical beam as the measurement probe, so there is no need to calibrate the measurement reference and the laser focus, which is otherwise required for other depth measurement methods, such as optical coherence tomography (OCT).

The controller 13 is operably coupled with the laser delivery system, the XY scan device 4, the Z scan device 8, detector 14 and the communication module 15. The controller 13 is configured to direct the laser delivery system to output the pulsed laser beam in a desired pattern at the focal point of the target in the eye so as to modify the target.

The controller 13, such as a processor operating suitable control software, is operatively coupled with the components of the system 1 to direct a fast scan line 12 of the pulsed laser beam along a scan pattern on or in the target material.

In some embodiments, the system 1 includes a beam splitter within the patient interface 9 and a detector 14 coupled to the controller 13 for closed-loop feedback control mechanism (not shown) of the pulsed laser beam. Other feedback methods may also be used, including but not necessarily limited to position encoder on the scanner 3 or the like.

In one embodiment, the pattern of pulses may be summarized in machine-readable data of tangible storage media in the form of a treatment table. The treatment table may be adjusted according to feedback input into the controller 13 from an automated image analysis system in response to feedback data provided from an ablation monitoring system feedback system (not shown). Optionally, the feedback may be manually entered into the controller 13 by a system operator.

The feedback may also be provided by integrating a wavefront measurement system (not shown) with the laser surgery system 1. The controller 13 may continue and/or terminate at least one incision in response to the feedback, and may also modify the planned sculpting based at least in part on the feedback. Measurement systems are further described in U.S. Pat. No. 6,315,413, the entire disclosure of which is incorporated herein by reference.

The communication module 15 provides information to the operator of the laser system 1 at the system and/or remotely via wired or wireless data connection. The communication module 15 may include a display device and input/output devices as known in the art to display information to an operator. An operator may control the system 1 via any known input control system including but not limited to a keyboard, a mouse, voice control, a motion sensing system, a joystick, and an eye-tracking system. The system 1 may be operated remotely and may also be monitored and serviced remotely.

Figure 1B:
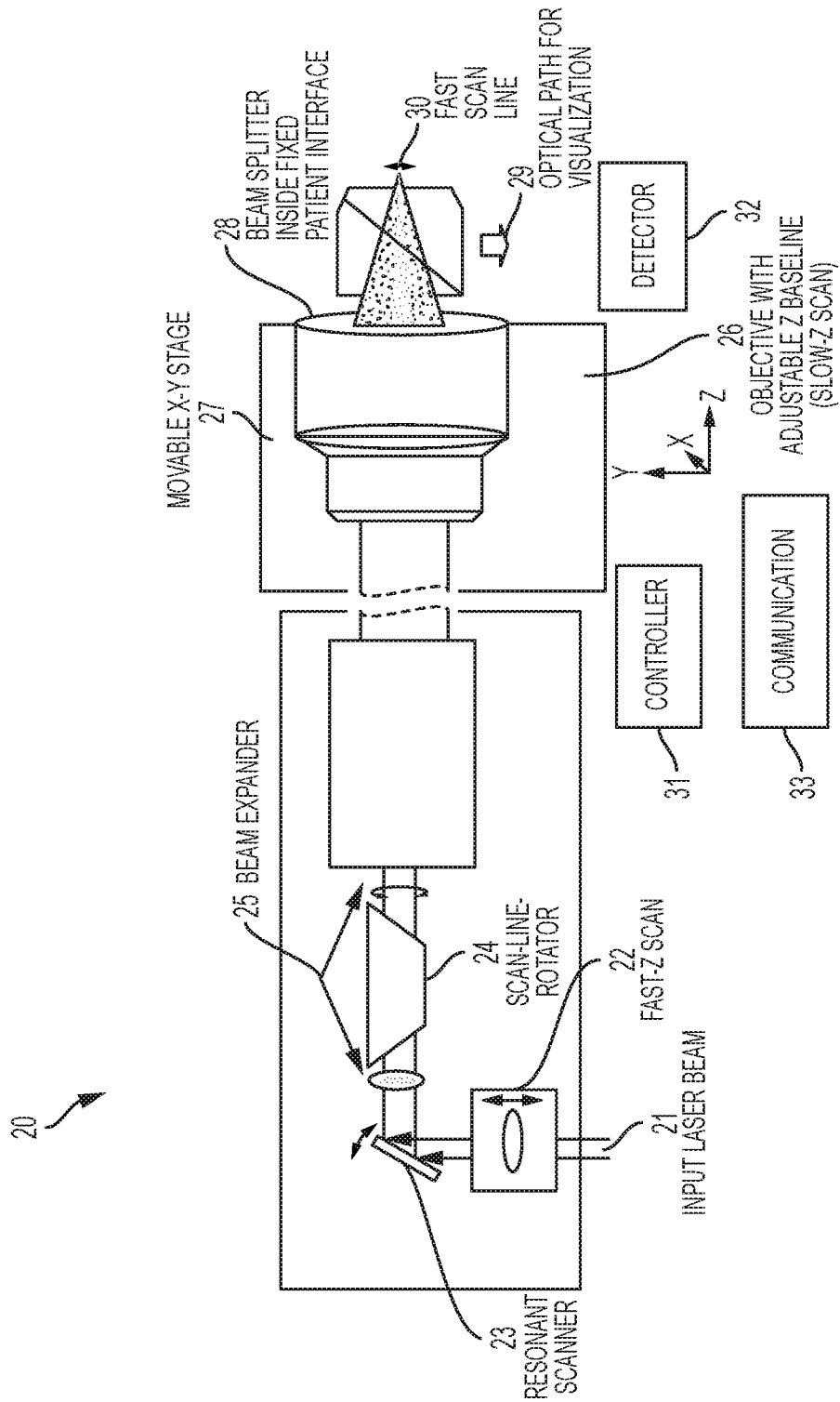

In another embodiment, FIG. 1B shows the beam delivery optics of a system 20. The system 20 includes, but is not limited to, an input pulsed laser beam 21 from laser source (not shown), fast-Z scan 22, a resonant scanner 23 for producing a fast scan line 30 of the pulsed laser beam 21, a scan line rotator 24 (e.g., a Dove or Pechan prism, or the like) for rotating the scan line 30, a beam expander 25, an objective 26 with an adjustable Z-baseline (slow-Z scan) 26, a moveable X-Y stage 27 for deflecting or directing the pulsed laser beam 21 on or within the target, a patient interface 28 that may include a beam splitter, an optical path 29, a controller 31, a detector 32, and a communication module 33. The slow-Z scan 26 sets the focus at a fixed depth and may set the Z-baseline. For example, the slow-Z scan 26 is stationary during a bed cut.

Some embodiments of the system are compact desktop systems that are placed on a table or the like. Other embodiments may include a motorized stage. The compact system allows a patient and patient interface to be oriented downwards, upwards, or in any direction, and not necessarily upright.

Figure 2A:
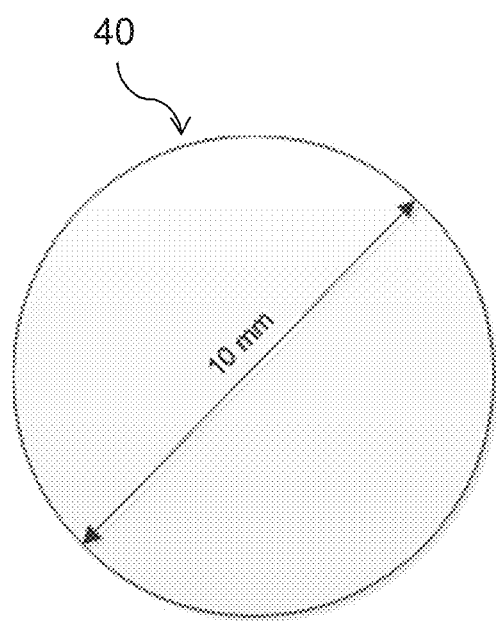
FIGS. 2A and 2B are simplified views of an optical field according to an embodiment of the present invention.

Next, FIG. 2A provides a simplified view of a surgical field 40. Typically, laser-assisted ophthalmic procedures are performed within a surgical field 40 of an eye that has a diameter of about 10 mm. Some of these systems utilize solid state femtosecond lasers including an oscillator, stretcher, amplifier and compressor. Conventional laser systems include a laser with optics large enough to generate a laser beam with an optical field that matches the surgical field. Scanning mirrors or other optics (not shown) may be provided to angularly deflect and scan the pulsed laser beam over the entire surgical field. These scanning mirrors may be driven by a set of galvanometers that further add to the bulk and complexity of conventional laser systems.

However, providing a sufficient numerical aperture (NA) to perform laser surgery requires large, expensive optics and a corresponding cumbersome, heavy and expensive beam delivery system. For example, an objective of the iFS Advanced Femtosecond Laser System alone weighs over 30 lbs. in order to allow a pulsed laser beam to scan freely within the 10 mm surgical field. These systems provide a practical maximum NA of about 0.4 due to the increasing cost, size and complexity of system components when NA is increased.

Figure 2B:
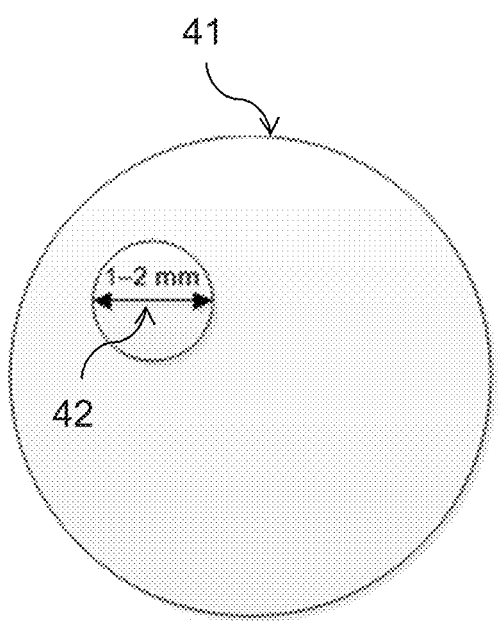

FIG. 2B illustrates an optical field 42 according an embodiment of the invention that is significantly smaller in diameter than the surgical field 41. The diameter of the optical field 42 depends on the length of the fast scan line 12 generated by the resonant scanner 3. For example, the diameter of the optical field 42 may be between 1 mm and 2 mm, and may preferably be 1.2 mm. This allows the laser to be made much smaller with laser beam tissue interaction in a low-density plasma mode.

For a given NA, the size and cost of the laser optics is reduced as the optical field is reduced in size. Consequently, increasing an NA value is significantly more cost effective for a smaller optical field. Since the optical field 42 may be about five to ten times smaller than the surgical field 41, a higher NA is achievable at a reduced cost compared to an optical field matching the surgical field 40. Accordingly, the invention provides higher NA at lower cost.

As shown in FIG. 2B, an optical field 42 does not by itself cover an entire surgical field 41. However, the optical field 42 is moved mechanically by the moveable XY device 7 across the entire surgical field 41. As will be described later, a resonant scanner 3 generates a very fast scan line within the optical field 42 that is oriented (rotated) within the optical field 42 by an XY scan device 4 and moved within the entire surgical field 41 by the moveable XY scan device 7. Reducing the size of the optical field significantly reduces the complexity, size, and weight of the laser source. Furthermore, an opto-mechanic arm mechanism is unnecessary in the laser system 1. in this manner, the laser optics are provided at a much lower cost with improved focus to achieve better surgical outcomes.

Embodiments of the invention may utilize a femtosecond oscillator or oscillator low energy laser. The laser source 2 may include an active medium fiber laser amplifier, oscillator and compressor, but need not include a stretcher. The laser source 2 may be fiber oscillator based, such as a diode-pumped fiber laser. The diode-pumped fiber laser may be a mode-locked fiber oscillator based laser having a single-mode, double-clad fiber oscillator and all positive dispersion elements.

The laser may generate a pulsed laser beam having a pulse repetition rate in the range between 5 MHz and 25 MHz, pulse energy in the range between 1 nJ and 5 µJ, a wavelength between the range of 1020 nm and 1065 nm, a pulse duration between the range of 10 femtoseconds and 10 picoseconds, a spot size between 0.2 µm and 2.0 µm (FWHM), and a numerical aperture NA between 0.25 and 1.3. An NA of 0.6 produces a 1.1 µm FWHM spot. The NA value is preferably provided between 0.25 and 1.0, more preferably between 0.4 and 1.0, and may be 0.6 in the illustrated examples.

Moreover, the reduction in size and complexity of the system 1 allows the laser delivery system to be configured to deliver the pulsed laser beam to the focal point of the target in the patient's eye while the patient is seated either in an upright position or in a reclining position.

Figure 3:
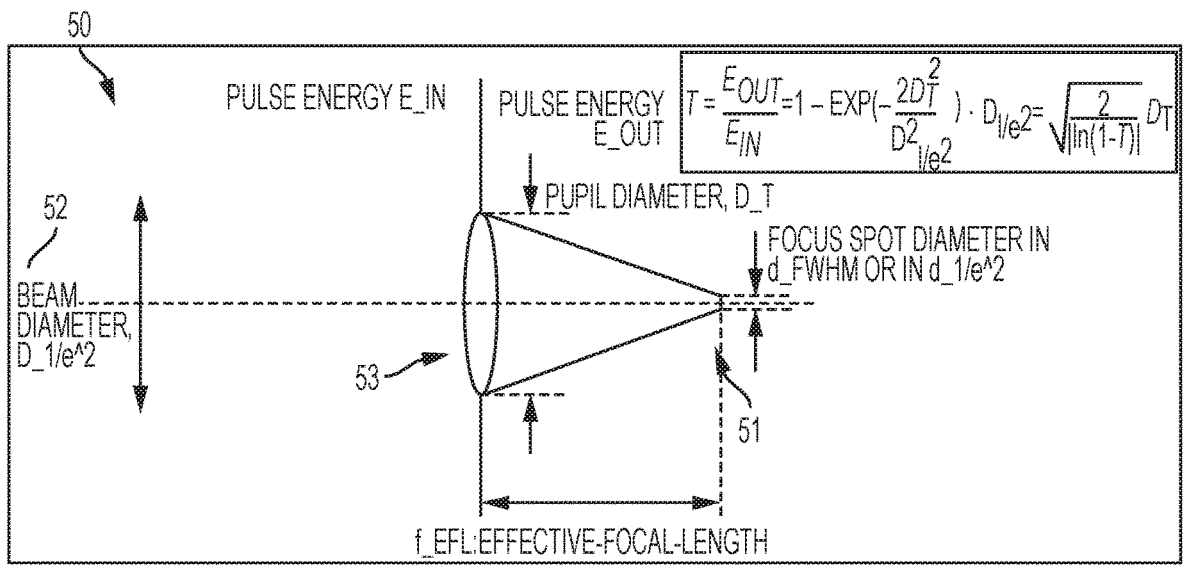
FIG. 3 is a diagram of a pulsed laser beam according to an embodiment of the present invention.

FIG. 3 is a diagram of a pulsed laser beam 50 including the relationship between the beam diameter, pulse energies, focus spot diameters and effective focal length. The focus spot 51 generated by a laser 2 may be provided at a focus point of the cornea to generate a bubble that separates and dissects tissue.

A pulsed laser beam directed at corneal tissue will first generate plasma. Additional pulses then generates a bubble in tissue. Finally, the bubble expands to generate tissue separation/dissection.

A pulsed laser beam applied to tissue first generates plasma, that then generates a bubble, and finally leads to tissue separation/dissection. A typical threshold value for tissue dissection is $10^{13}$ W/cm$^2$. To perform tissue dissection, a pulsed laser beam needs to reach or exceed this threshold value determined by the equation $\varepsilon/\tau\sigma$, where $\varepsilon$ is the energy of the beam, $\tau$ is the pulse width, and $\sigma$ is the area of the beam.

Based on this relationship, for a given amount of energy, decreasing the spot size will increase the optical density of the beam since the same amount of beam energy is concentrated in a smaller area. Likewise, as the spot size of the beam decreases, the amount of energy of the beam may be reduced while still exceeding the tissue dissection threshold value. A smaller amount of beam energy applied in a smaller area results in a finer tissue cut.

An inverse relationship exists between spot size and numerical aperture such that as NA becomes larger, a spot size 51 becomes smaller. Numerical aperture represents the sine of the half angle of the cone of a laser beam. Accordingly, a higher NA value is desirable in providing a finer cut.

For example, the laser system 1 outputs an energy level of 0.14 µJ that is 20% of the energy level output of 0.7 µJ from the iFS Laser System. Similarly, the system 1 provides a pulse width of 120 fs and area of $\pi \cdot 0.5^2$ µm$^2$ while the iFS Laser System provides a pulse width of 600 fs and area of $\pi \cdot 0.8^2$ µm$^2$.

Figure 4:
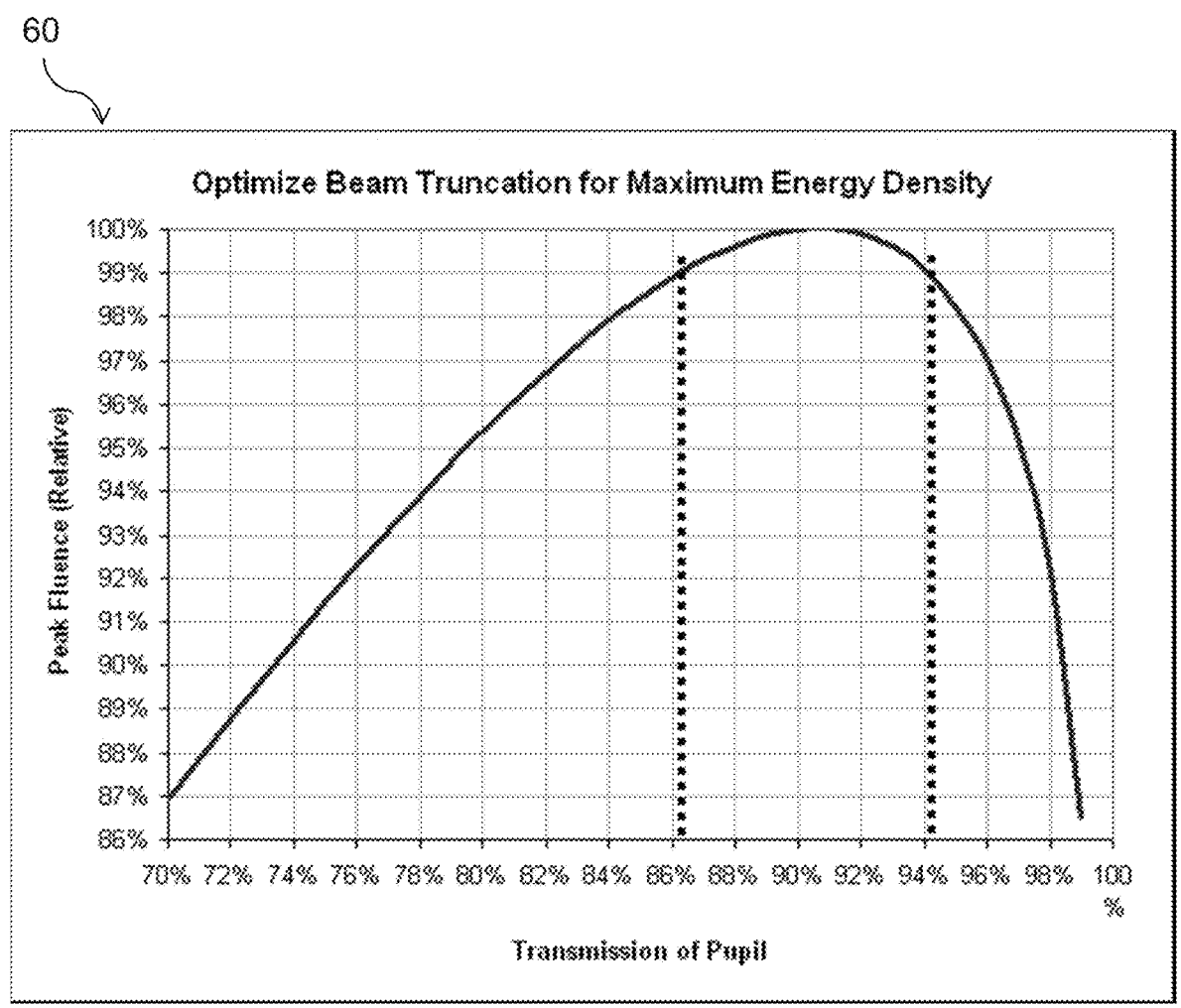
FIG. 4 is a graph related to laser beam optimization according to an embodiment of the present invention.

FIG. 4 is a graph 60 related to laser beam optimization. As illustrated in FIG. 3, a beam diameter 52 may be different from the diameter of a lens 53 that focuses the light pulse into a focus spot 51. Selection of a beam diameter 52 smaller than the lens diameter 53 ensures that all of the light energy passes through the lens. However, an inverse relationship exists between a beam diameter and a focus spot size such that the focus spot size will increase as the beam diameter decreases. $F_{PEAK}$ represents energy area density and T represents energy transmission.

Similarly, laser overfield is a configuration where the beam diameter is greater than the lens diameter 53 such that a portion of the light energy is not transmitted through the lens and lost. However, the loss in energy efficiency by laser overfield does provides the benefit of a smaller focus spot size 51.

In balancing the factors of energy efficiency and spot size, FIG. 4 illustrates the optimal conditions to attain maximum energy density. In particular, a maximum peak fluence is achieved with about a 10% loss of transmission. In other words, the optimum ratio of energy transmission to spot size occurs when the pulsed laser beam diameter is about 10% larger than the lens diameter.

A laser as described above may operate at very high frequencies such as on the order of 10 MHz (or 10,000,000 pulses/sec). Laser pulses that are not scanned will be directed at a single point which is unsuitable for ophthalmic procedures. Therefore, a scanner is needed to operate at a sufficient frequency to scan these pulses across a surgical area.

The scanner 3 of the system 1 may be a high frequency resonant optical scanner having a fixed frequency in a range between 3500 Hz and 21,000 Hz. In an preferred embodiment, a 7910 Hz resonant scanner is implemented. Use of a resonant scanner is particularly effective as they have no wearing parts, are reliable, cost-effective and compact (e.g., 1.0"W×0.7"D×2.5"H). The resonant scanner 3 produces a line raster pattern with a length of the raster pattern between 0.5 mm and 2 mm. In some embodiments, the resonant optical scanner is configured to scan the pulsed laser beam from the laser delivery system in a line.

Figure 5:
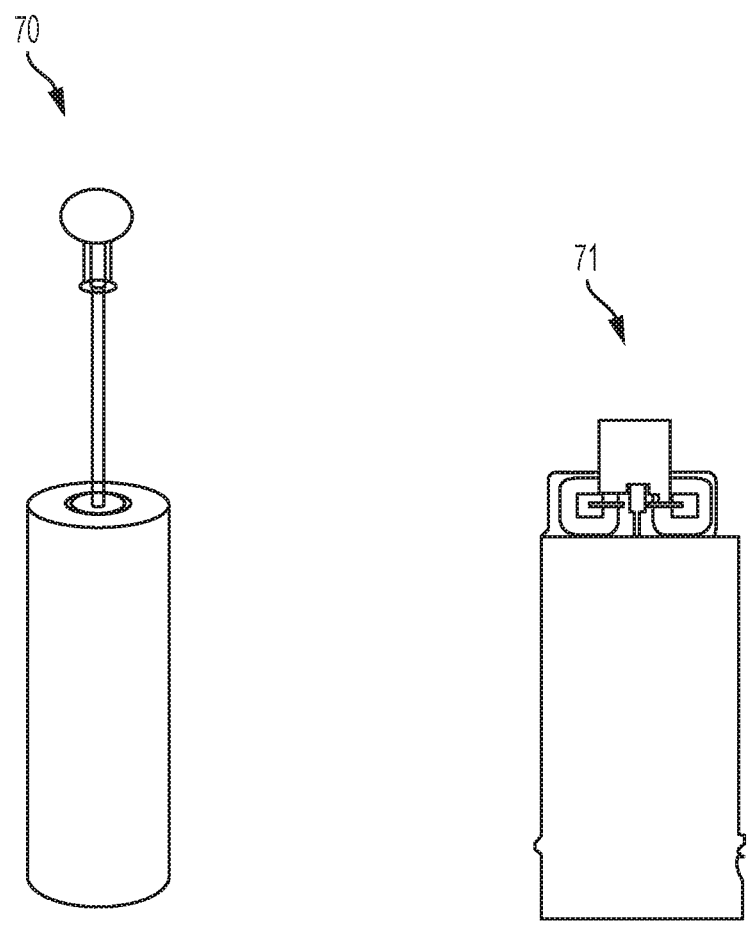
FIG. 5 illustrates resonant scanners according to embodiments of the present invention.

FIG. 5 illustrates exemplary resonant scanners 70 and 71 that include a mirror attached to a metal rod that vibrates at an inherent resonant frequency. The shape and composition of the rod are selected to operate at a desired frequency to scan laser pulses. The resonant scanner 3 does not require a plurality of mirrors or a set of cumbersome galvos to scan across a surgical field as other systems do. Instead, the scan line may be rotated by a scan line rotator within an optical field and the scanner 3 may be scanned across a surgical field by a moveable XY stage. In some embodiments, the resonant scanner 3 provides an order of magnitude in weight and cost savings over the scanner system provided in the iFS Laser System. The resonant scanner 3 may scan at a rate of about 20 m/s while the iFS scanner scans at a rate of about 3 m/s.

Figure 6:
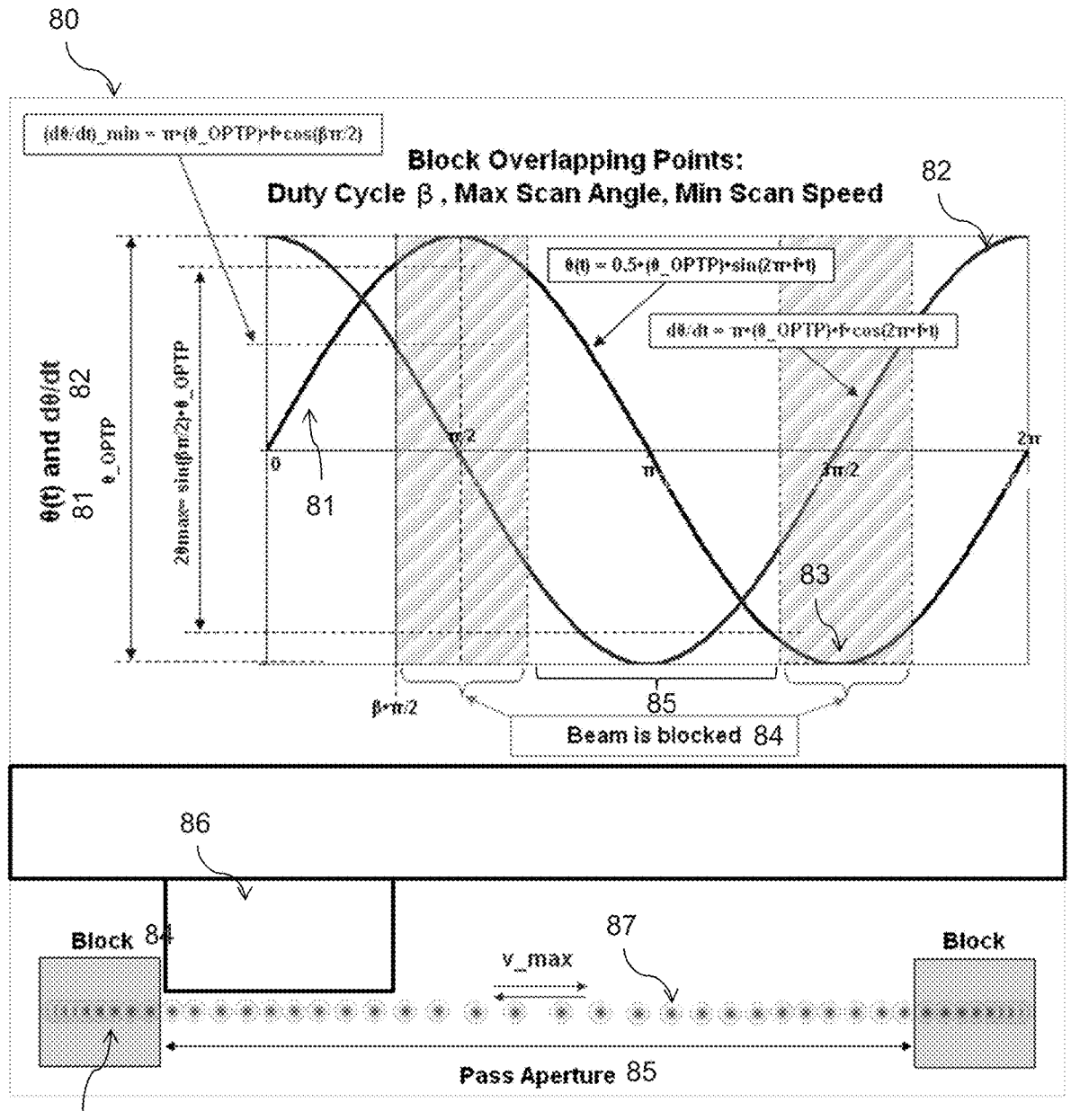
FIG. 6 is a graph related to resonant scanning operation according to an embodiment of the present invention.

As illustrated in the graph 80 of FIG. 6, the scanning provided by a resonant optical scanner 3 is characterized by a sinusoidal curve. The resonant optical scanner may oscillate at a frequency between 200 Hz and 21000 Hz. The curve 81 represents the scanning angle of a resonant scanner 3 and curve 82 represents the scanning speed. As shown by the curve 82, the scanning speed continually varies such that the density of laser spots along the scan line will vary. Accordingly, that the distribution of laser pulses is uneven.

For instance, scan line 86 illustrates the sinusoidal distribution of laser spots provided by a resonant scanner 3. Whether a scanning speed reaches zero or a maximum speed, laser pulses will continue to be emitted at the same rate. Undesirable spot overlapping 83 occurs when the scan speed is at and near zero. This may lead to areas of tissue that are overcut from an excess number of laser pulses.

Some embodiments of the invention overcome this by preventing overlapping spots 83. In one embodiment, the overlapping spots 83 are emitted but physically blocked 84 from scanning a target material to provide a higher quality tissue cut.

Figure 7:
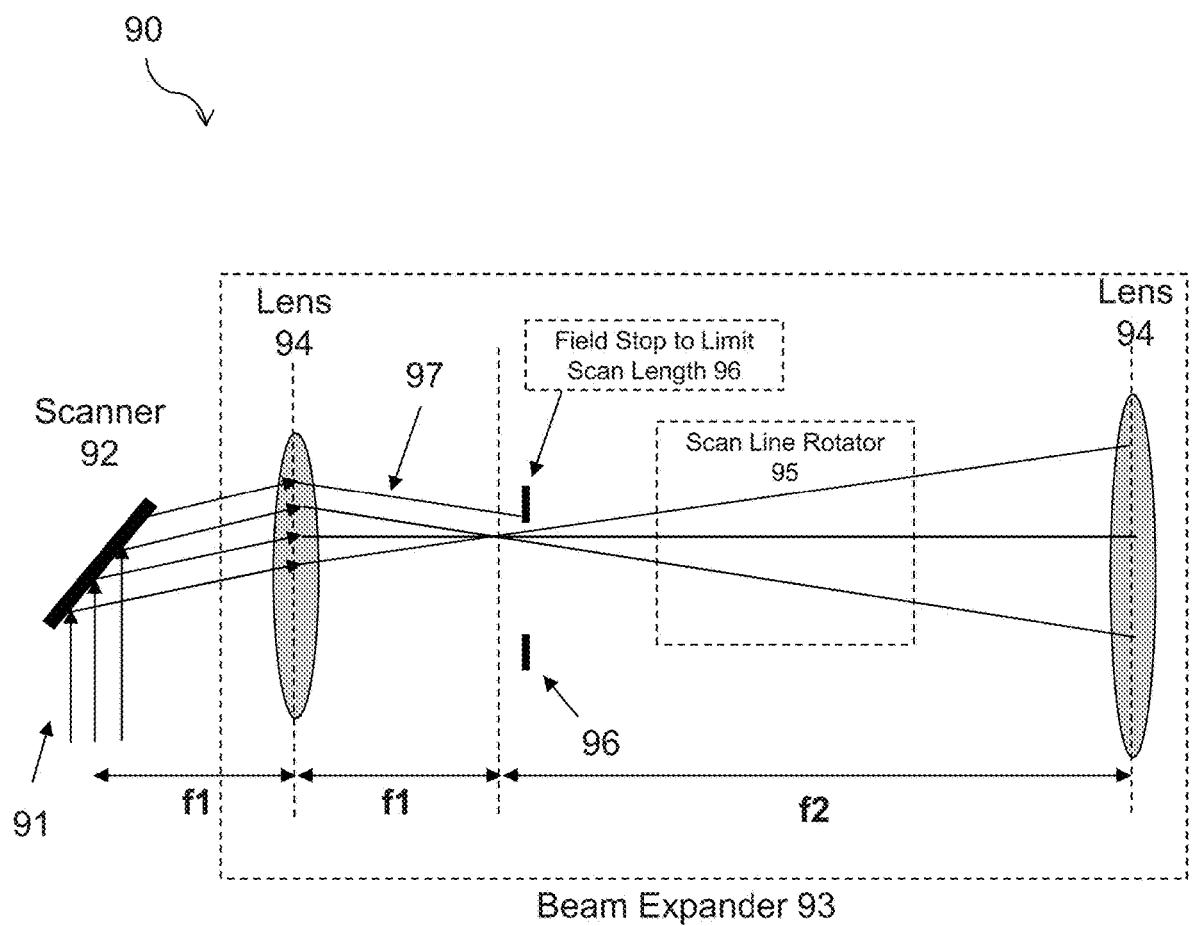
FIG. 7 illustrates a schematic view of a beam delivery system according to an embodiment of the present invention.

FIG. 7 illustrates a schematic view of a beam delivery optics system. A pulsed laser beam 91 emitted by a laser source (not shown) reaches a resonant optical scanner 92 and is delivered into a beam expander 93. The beam expander includes a lens 94 that focuses the beam through a scan line rotator 95 and another lens 94. A predetermined portion 97 of the beam 91 is blocked by a field stop 96 to limit the scan length of the raster.

The pulses 97 may, for example, correspond to the blocked portion 84 overlapping spots 83 in FIG. 6. In this manner, undesirable light pulses are physically blocked within a beam expander 93 as the light focuses, ensuring that laser spots are not concentrated too densely within a spot or scan line area. The blocker or field stop 96 may be provided near but not precisely at the focal plane so as to prevent the blocker from burning. It is noted that conventional scanners do not exhibit sinusoidal wave characteristics such that those systems have no need to provide blocking.

Figure 8:
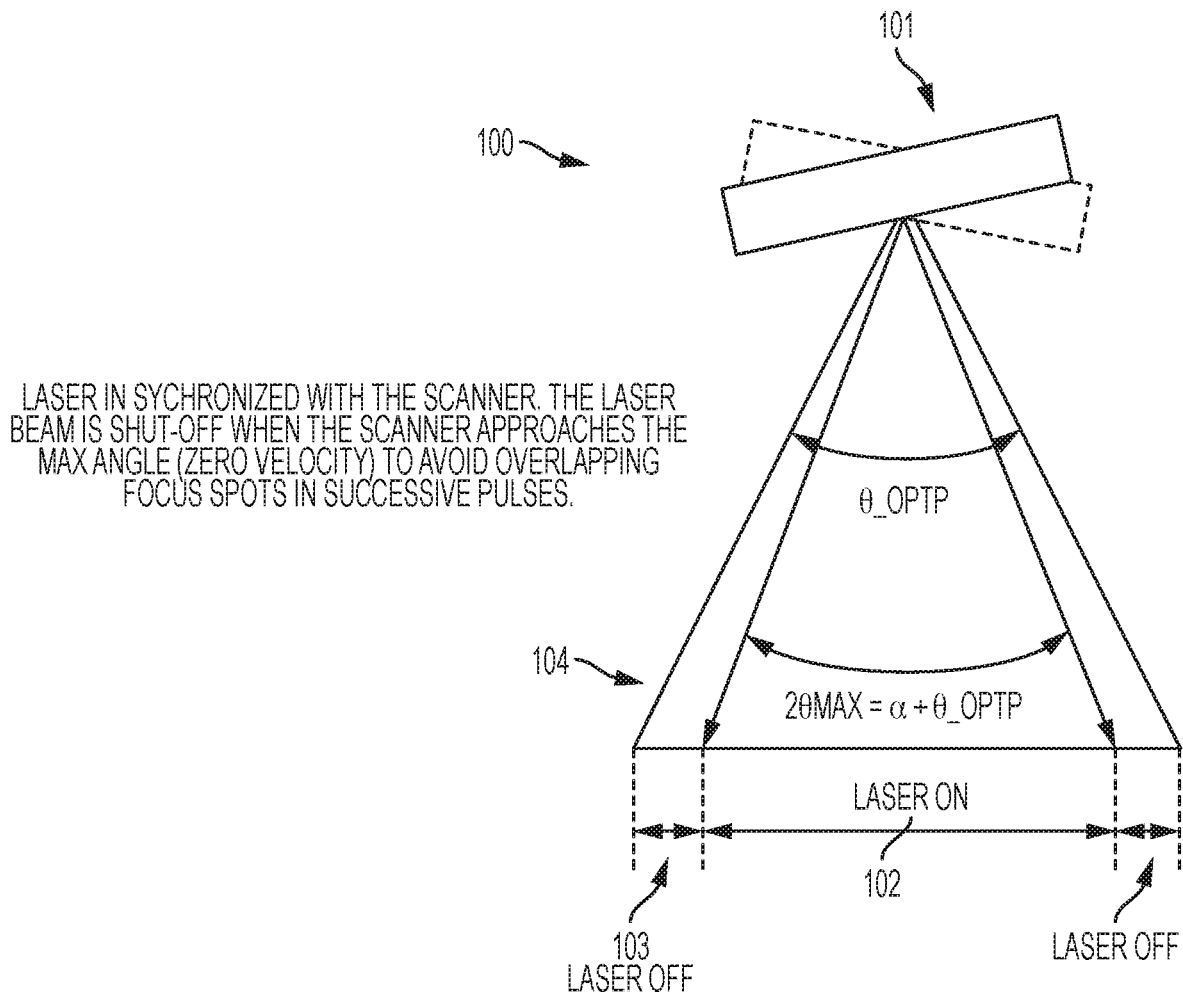
FIG. 8 illustrates a schematic view of a scanner according to an embodiment of the present invention.

In an alternative embodiment, FIG. 8 illustrates a schematic view of a scanning system 100. A resonant optical scanner 101 is illustrated as vibrating so as to produce a scan line 104. A laser (not shown) producing laser pulses is synchronized with the frequency of the scanner 101 such that the laser is turned on 102 and off 103 when the scanner 101 approaches a predetermined maximum scan angle with a corresponding zero velocity in order to prevent overlapping focus spots in successive pulses.

Equation 1 is an algorithm for determining a duty cycle that is a percentage time that a beam passes an aperture, scanner frequency, optical peak-to-peak angle, a pupil diameter for given laser pulse repetition rate, and desired numerical aperture of the optical system. An example for NA=0.6 is provided below:

$$2400 \cos\left(\frac{\pi}{2}\beta\right)[\theta_{OPTP} \cdot f_{SCAN} \cdot D_{PUPIL}] \geq f_{LASER} \quad \text{(Eq. 1)}$$

Figure 9:
FIG. 9 is a table of scanner parameters according to an embodiment of the present invention.

Equation 1 guides the selection of resonant scanner parameters for a spot edge to edge condition, as shown in Table 110 in FIG. 9. Table 110 highlights the values that satisfy a requirement of spot size (FWHM=1.1 um) and avoiding laser spot overlap.

Figure 10:
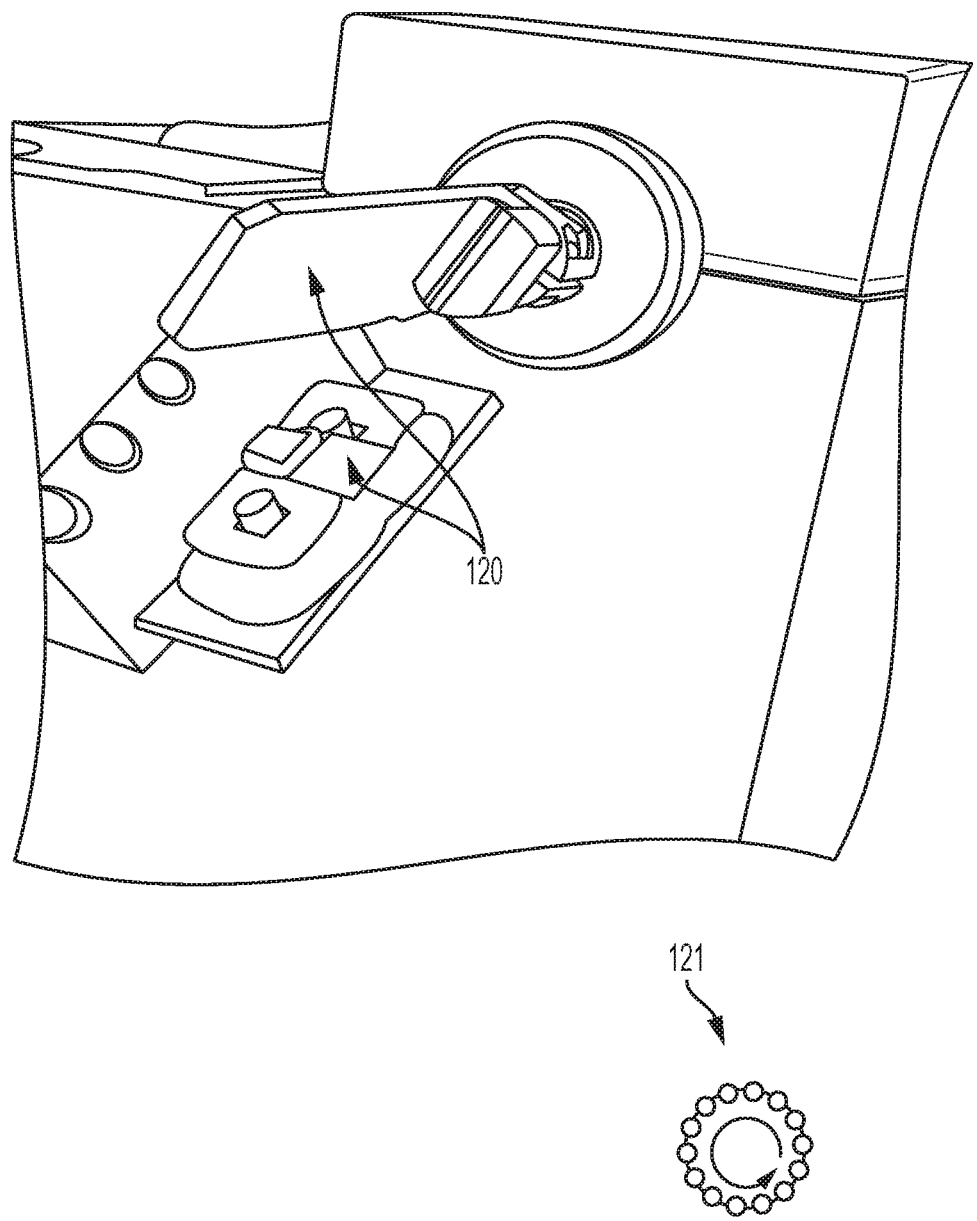
FIG. 10 illustrates a perspective view of a scanner system according to an embodiment of the present invention.

In some embodiments, a fast raster scanning pattern can be generated by synchronizing a plurality of resonant scanners in the laser system 1. For example, FIG. 10 illustrates a pair of perpendicular scanning resonant mirrors 120 with the same frequency, the same amplitude, and a phase difference of 90° between them that generate a fast circular scan line 121, for example.

A circular scan line exhibits a number of advantages including equal spot distribution so as to render blocking techniques redundant. In this case, the linear speed of the scanning is a constant, and is equal to the maximum speed that can be achieved with a single scanner. Therefore, there is no need to block the "zero speed" points as in the case of using a single scanner, and the duty cycle is 100%, i.e., 100% of laser pulses will be used for tissue dissection. Furthermore, a circular scan line ensures that targeted tissue receives two pulses with each pass, thereby ensuring a cut. Also, a circular scan line is also well matched against another curve, such as the edge of a circular surgical field.

The first scanner may be provided for the x axis while the second scanner may be provided for the y axis in different phase relation to generate a plurality of two-dimensional scan patterns that may obviate the need for a scan line rotator. The use of at least two scanners may generate a line oriented at any desired angle, circle, curve, etc.

Another arrangement of synchronization is to synchronize two parallel scanners so that the optical peak-to-peak angle is doubled in comparison with a system using one resonant scanner. In yet another embodiment, a plurality of resonant scanners may be synchronized to extend the scanning range of a single scanner.

Next, embodiments of a scan line rotator will be discussed. A resonant scanner produces a one dimensional scan line in a single direction. However, this output is not ideal for cutting near an edge or curve of a surgical field. For example, when an optical field is provided along an edge of surgical field, the line must be rotated to fit the curve. Therefore, a scan line rotator is configured to rotate the scanned line in a desired orientation.

Figure 11:
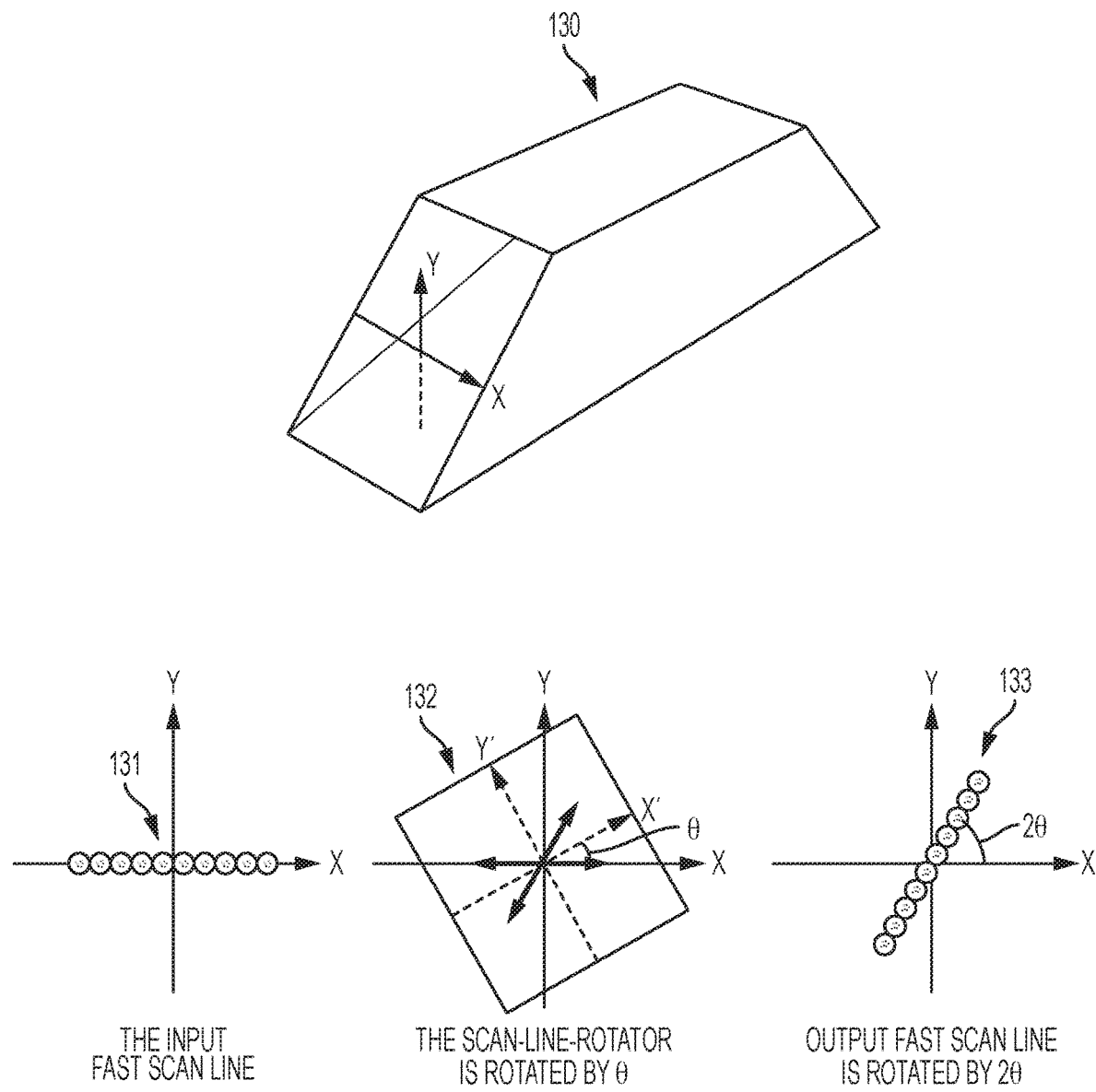
FIG. 11 illustrates a perspective and graphical view of a scan line rotator according to an embodiment of the present invention.

FIG. 11 illustrates a perspective view of an exemplary scan line rotator 130 and graphical views of a scan line rotated by a scan line rotator. The scan line rotator 130 is a Dove prism, but may also be a Pechan prism or a set of mirrors. Implementations of a scan line rotator using a Dove prism or Pechan prism are cost-effective, compact and lightweight, and contribute to a compact laser system. The input scan line 131 is a non-rotated scan line. As the scan line rotator 130 rotates by an angle θ, the input scan line 131 will follow the rotation and the output scan line will be rotated by 2θ.

The output raster 133 is thus oriented in any desired direction to scan an entire optical field. In combination with an XY stage, the system 1 may scan an entire treatment area. Tissue fibers may sometimes be aligned in certain directions that favor a rotated raster. Furthermore, a scan line rotator allows for flap creation, cornea incisions, IEK, inlays, rings, etc. and procedures such as SmILE or ReLEx.

Figure 12A:
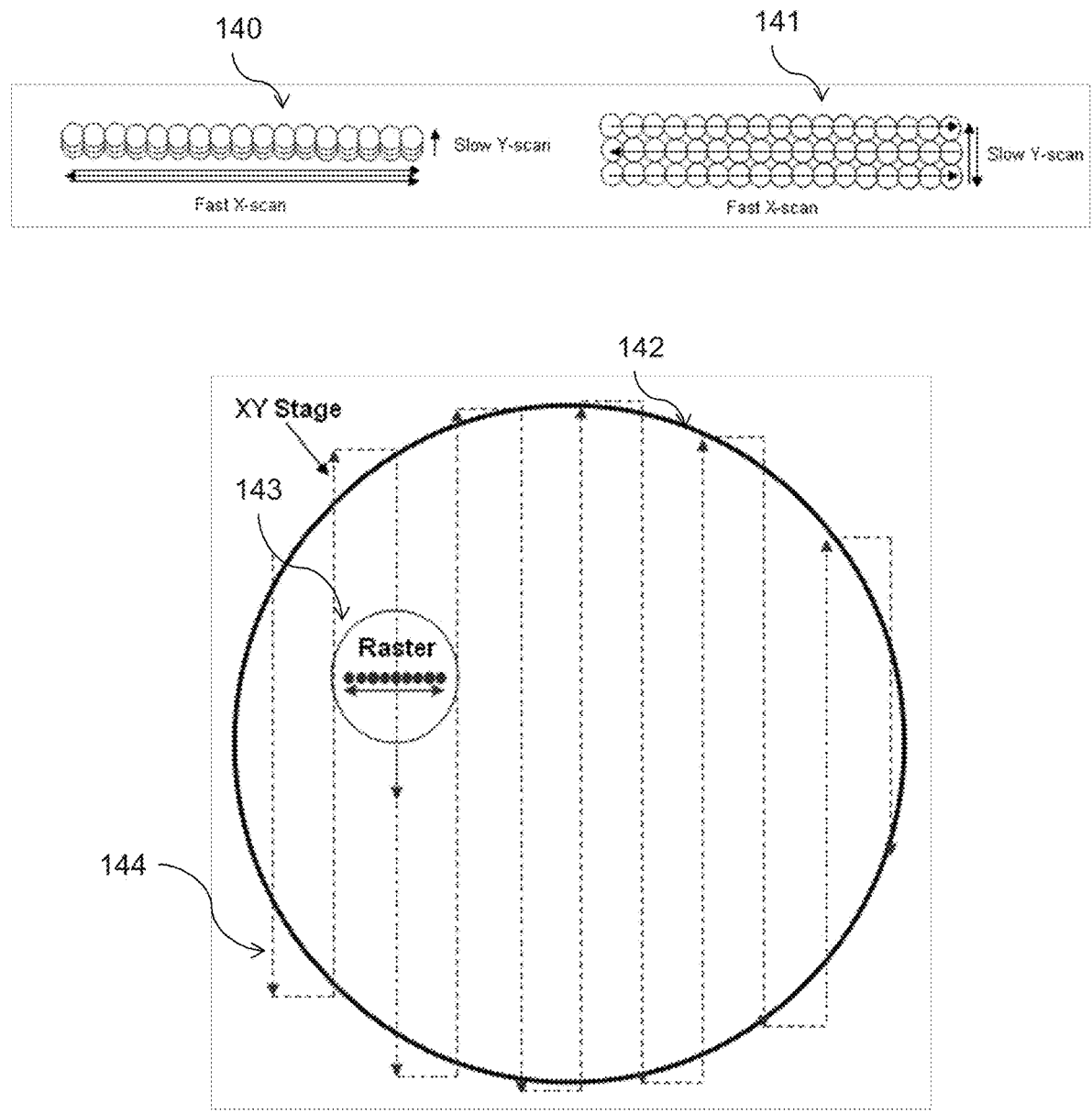
FIGS. 12A-12C illustrate bed cut scanning patterns according to an embodiment of the present invention.
Figure 12B:
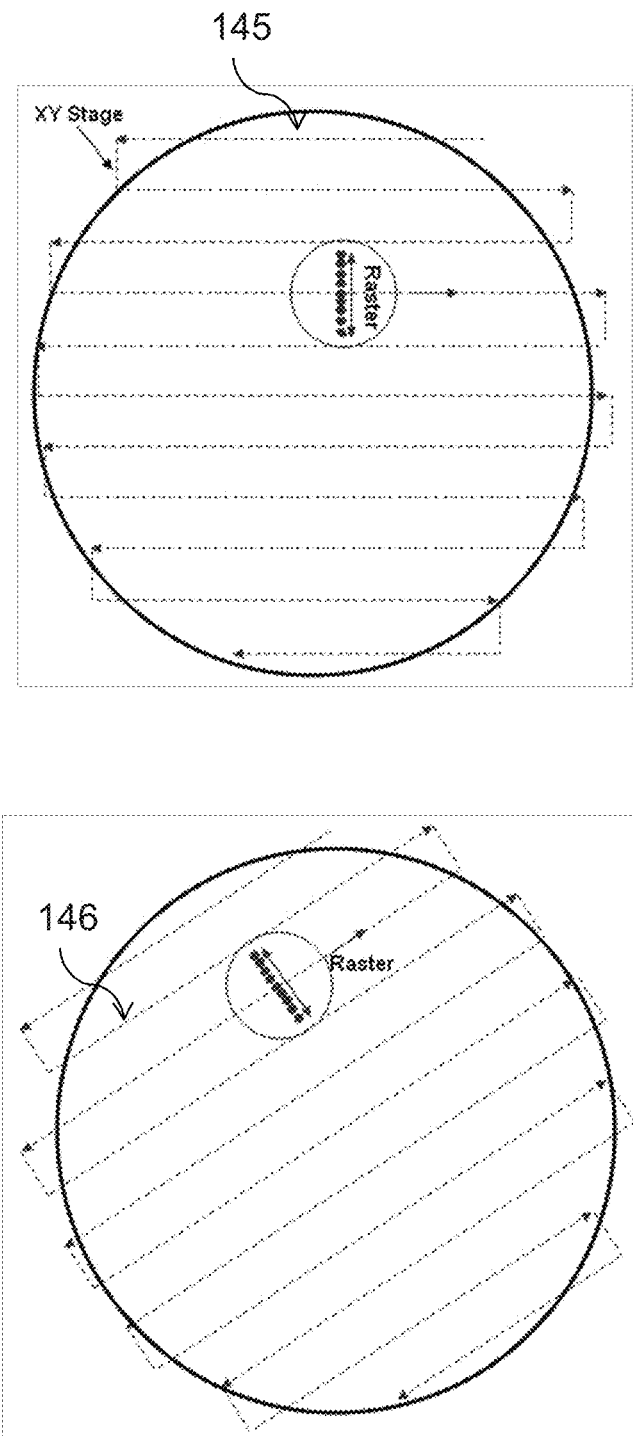
Figure 12C:
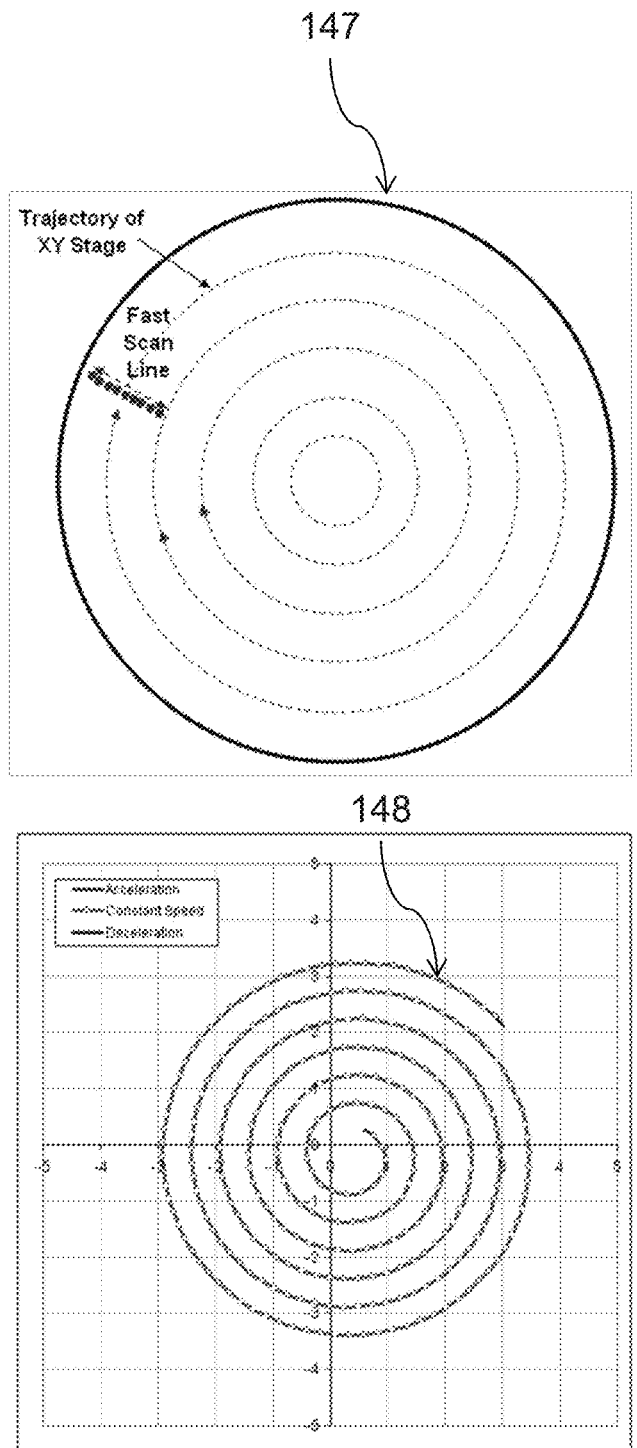

FIGS. 12A-12C illustrates scanning patterns provided by an XY stage 7. The XY stage 7 moves the optical field and raster line across a surgical field. Raster line scanning patterns 140 and 141 may be provided in a number of configurations, as illustrated in FIG. 12A. For example, in order to cover an intended lamellar dissection area 142, the XY stage 7 may move the raster line 143 up and down systematically across the surgical field along path 144 to cover the full flap bed and provide a bed cut. The width of each pass may be selected so as to provide overlapping cuts where tissue is cut a plurality of tunes by the raster.

FIG. 12B illustrates other scanning patterns of the XY stage 7 that may move the raster line horizontally along a path 145 across the surgical field, as well as along a path 146 at a predetermined angle. The raster may be aligned perpendicularly with the movement of the XY stage, for example. FIG. 12C illustrates a circular path 147 and a spiral path 148 that each cover an entire predetermined treatment area.

Figure 13:
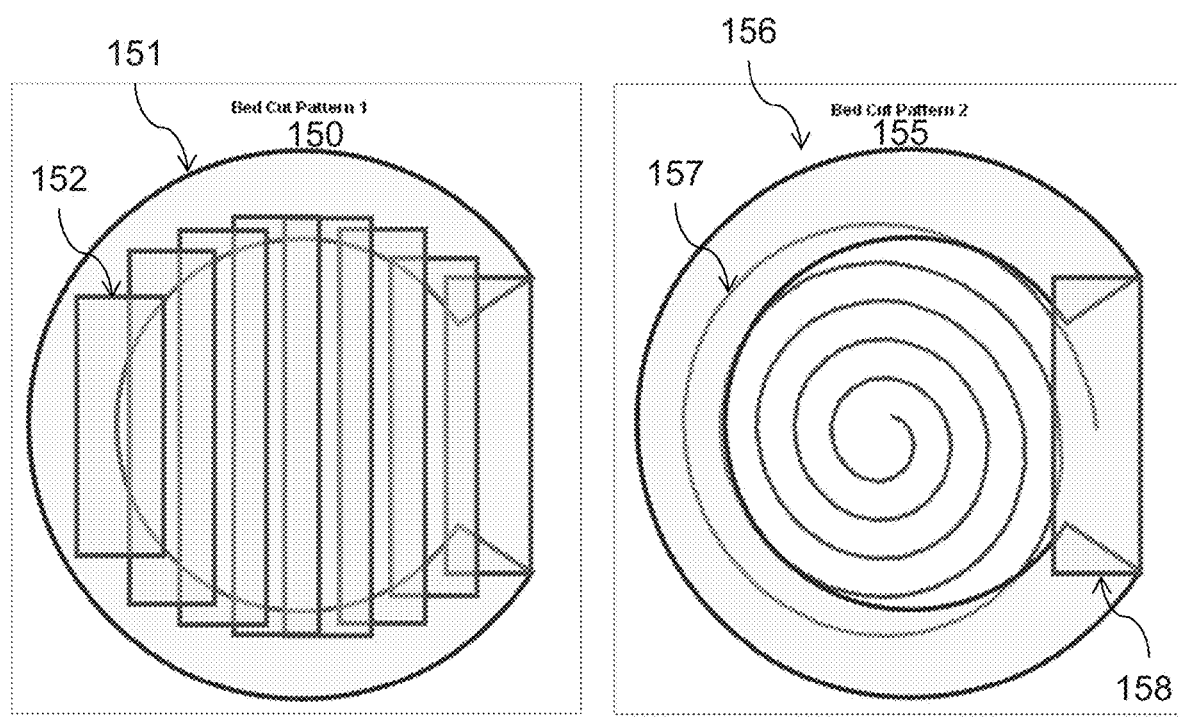
FIG. 13 illustrates bed cut scanning patterns according to an embodiment of the present invention.

Turning to FIG. 13, combinations of the above scanning patterns may be provided within a surgical area. A first bed cut pattern 150 includes an annulus scan 151 and a set of linear (rectangular) scans 152 that ensure that every portion of the treatment area has been scanned by the optical field. Similarly, a second bed cut pattern 155 includes an annulus scan 156, a spiral scan 157 and a rectangular scan 158.

Figures 14A, 14B:
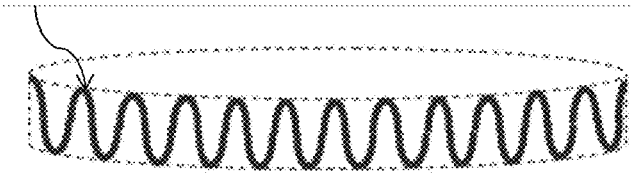
FIGS. 14A-14B illustrate side cut scanning patterns according to an embodiment of the present invention.

Next, FIGS. 14A-14B are directed to side cuts. A fast Z scan device 8 modifies a depth of focus of the pulsed laser beam. Some embodiments of the fast Z scan device 8 are realized through a voice coil that drives a lens. When the lens moves, the curvature of the beam is changed, leading to focus a depth change. The z-scan frequency may be between 50 Hz and 15,000 Hz. With a fast Z scan device and X-Y stage, a 90° side-cut can be generated where 0° is defined as the radial direction in the lamellar cut bed. A 90° side-cut can be applied for flap creation, for example.

In FIG. 14A, a scan line is moved along a path 160 sinusoidally in a depth direction by the fast Z scan device and circularly by the X-Y stage to produce a vertical slice. FIG. 14B illustrates another path 161 generated by a low Z scan frequency. A side cut 162 is generated by a linear raster 163 generated by a resonant scanner. The raster line is moved 164 up and down by the fast Z scan device along a circumference by an X-Y stage. Rotation of the scan line by a scan line rotator ensures that the raster 165 is kept tangential to the circumference during a side cut.

For example, for a 9.5 mm diameter flap, 20 MHz laser repetition rate, 10 kHz raster scan with 1 mm scan length, an 85 Hz Z-scan frequency and +/−60 µm Z-scan amplitude may be provided. The side-cut may be completed within one second, during which the raster scan passes any given location five times to ensure tissue separation. The side cut need not be vertical and may also be angled to better match the tissue.

Figure 15:
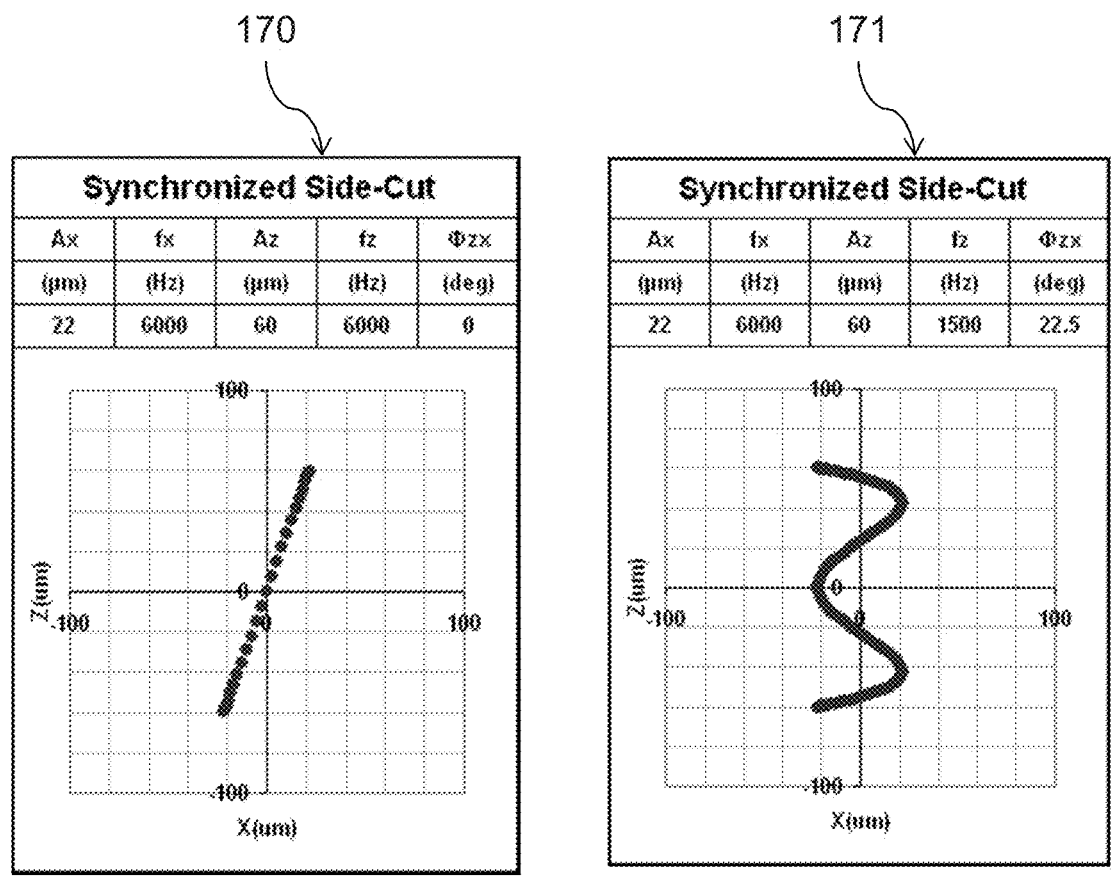
FIG. 15 illustrates synchronization according to an embodiment of the present invention.

Turning to FIG. 15, synchronization between a resonant scanner and fast-z voice coil scan is illustrated. Let a raster scan be described by Equation 2:

$$X(t) = A_X \cdot \sin(2\pi \cdot f_X \cdot t) \quad \text{(Eq. 2)}$$

$A_X$ is the adjustable amplitude of the raster on the focal plane, and $f_X$ is the fixed resonant scanner frequency. The fast-z scan may be described by Equation 3:

$$Z(t) = A_Z \cdot \sin(2\pi \cdot f_Z \cdot t + \Phi_{ZX}) \quad \text{(Eq. 3)}$$

$A_Z$ is the adjustable amplitude of the z-scan at the focus, $f_Z$ is the adjustable fast-z scan frequency, and $\Phi_{ZX}$ is the adjustable relative phase between the fast-z scan and the resonant scanner.

A variety of side-cut patterns may be produced by adjustment of the parameters $A_X$, $A_Z$, $f_Z$, and $\Phi_{ZX}$. For example, FIG. 15 illustrates a 70° side-cut 170 and an "M" shape side-cut 171 which increases a contact surface. Synchronization provided in this manner allows for a plurality of three-dimensional laser patterns for tissue dissection and for other light-assisted effect such as refractive index modification.

A plurality of incision patterns combining the aforementioned bed cut and side cuts may thus be generated, including an xy lamellar dissection, a spiral lamellar dissection, a vertical side-cut, a plano-vertical side cut, an intrastromal incision, a lenticular incision, as well as any three-dimensional dissection. Other cuts include a flap cut for LASIK, lens cut for myopia correction, ring resection for inlay, arcuate incision for astigmatism, clear cornea incision for a cataract entry cut, penetrating cut for cornea transplant, anterior and posterior deep lamellar cut for cornea transplant, corneal ring cut for insertion of stiffening material, pocket cut to treat presbyopia, intralase enabled keratoplasty (IEK) for corneal transplants, and so forth.

Next, an optimal sequence of cutting is described. A byproduct of tissue dissection is the release of gas. If gas from laser tissue dissection has nowhere to vent, the gas will penetrate back into the tissue and create an opaque bubble layer that will hinder the dissection of tissue beneath that layer. Embodiments of the invention herein eliminate the opaque bubble layer by providing a channel for gas to escape during tissue dissection.

First, a side cut is performed in the Z plane that will also serve as a venting channel for gas to escape from the cornea. Next, a ring cut is performed in the XY plane. Gas emitted from the ring cut will pass through the side cut and out of the cornea. Finally, a band cut (e.g., rectangular cut, spiral cut) in the XY plane is performed with the gas generated therein escaping via the side cut via the ring cut channels created. A bed cut refers to the combination of the ring cut and rectangular cut or spiral cut. This sequence of cuts ensures that the generated gas has a channel to escape from the cornea so as to reduce or eliminate an opaque ring bubble layer.

Since a band cut is provided on the same plane as a ring cut, gas from the band cut will pass through ring cut, which will then pass through the side cut, thus providing a gas vent throughout the entire procedure. Furthermore, this procedure effectively eliminates the need for the creation of a "pocket" in a flap cut. Prior art approaches perform cutting in the opposite sequence and require another cut (pocket) whose sole purpose is to provide the air channel.

Figure 16A:
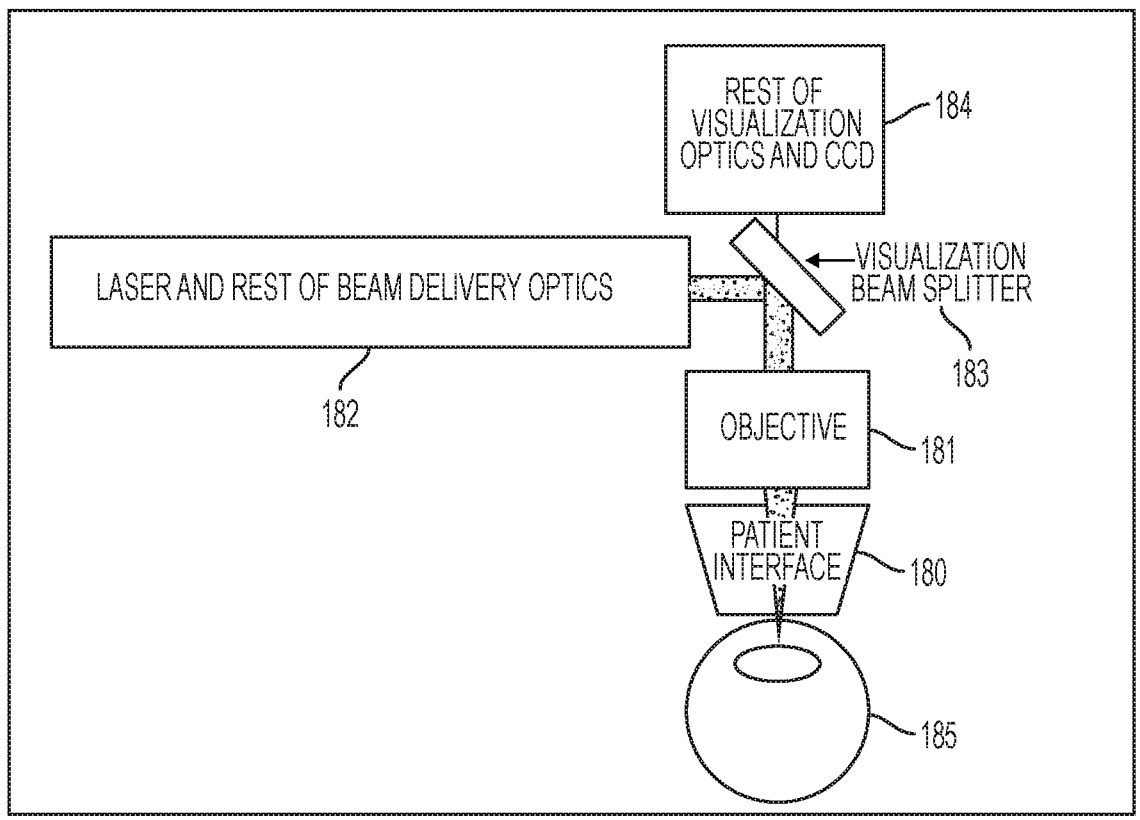
FIGS. 16A-16C illustrate prior art patient interfaces.
Figure 16B:
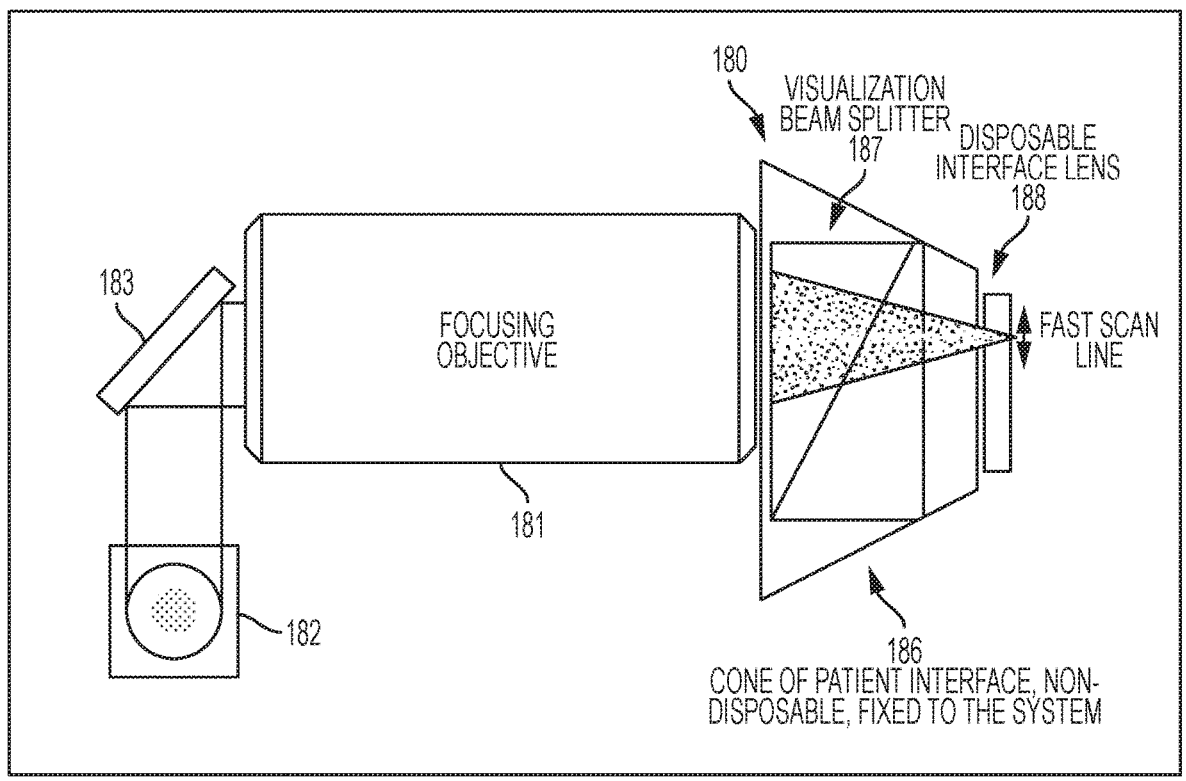
Figure 16C:
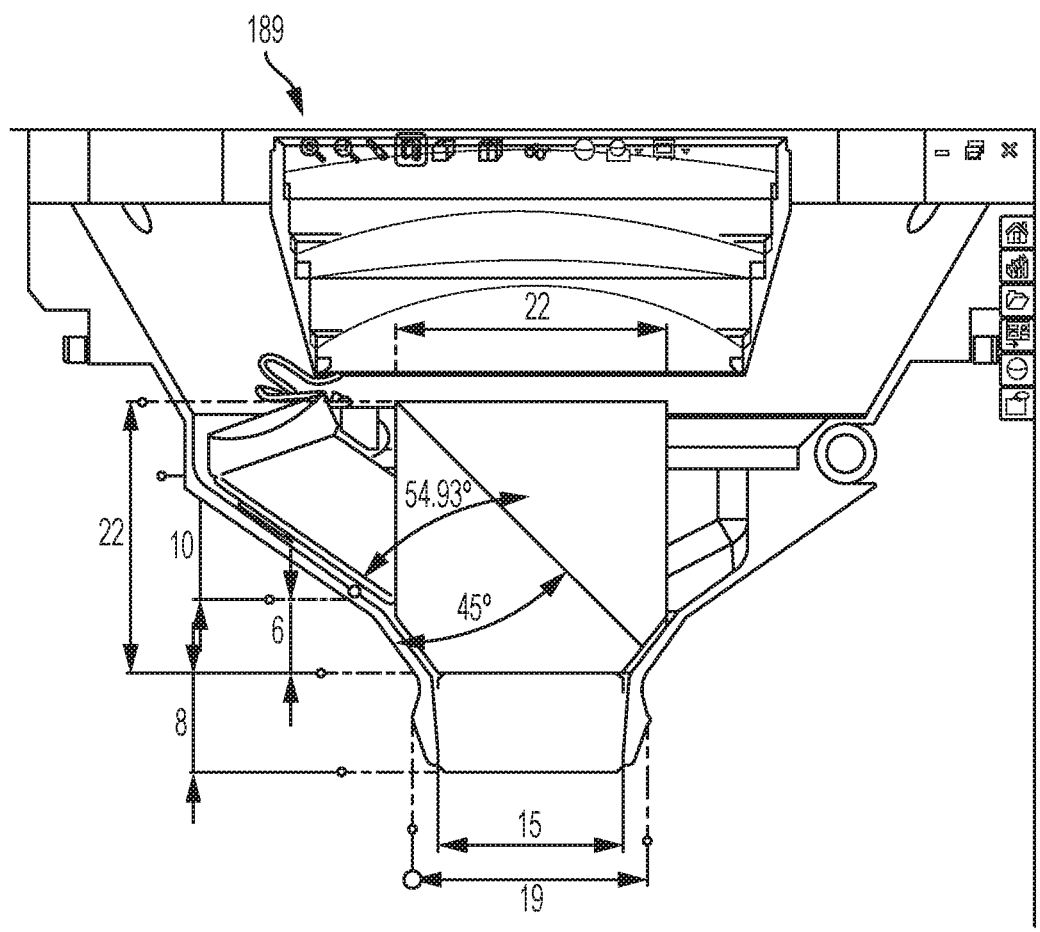

FIGS. 16A-16C illustrate a prior art patient interfaces according to an embodiment of the present invention. For many prior art femtosecond laser workstations, the field of view for visualization optics 184 such as a CCD and video microscope is similar to the field of view of surgical beam scanning such that a visualization beam splitter 183 is positioned above the focusing objective 181, patient interface 180, and cornea 185. In this configuration, the size of the optics system, including both beam delivery 182 and visualization 184, is generally large and unwieldy.

FIG. 16B is a schematic cross-sectional view of the patient interface 180 that includes a cone 186 that is fixed to the system, a visualization beam splitter 187, and a disposable patient interface lens 188. A beam splitter 187 is coated for reflecting the visual spectrum but passes light for the femtosecond laser wavelength and is placed inside the cone frame 186 of the patient interface 180 fixed to the system. The ocular video microscope optical path goes through this beam splitter. Accordingly, a cutting process may be viewed and/or displayed in-situ.

FIG. 16C is a cross-sectional view of another patient interface 189 where a visualization beam splitter is placed inside the cone of the patient interface 189. This design is sufficient for a limited range of numerical aperture of surgical beam, for example, NA≤0.4. For yet greater NA, such as NA=0.6, some Oblique rays of the surgical beam will experience high loss at the beam splitting surface (the 45° surface as shown in the diagram). As the NA increases, the size of the beam splitter will need to increase as well.

The visualization optical path may be provided outside the cone of the patient interface in a side channel. However, for deep set eyes, the side channel has to be placed much higher, increasing the size and bulk of the beam splitter. Consequently, the outer dimension of the patient interface cone will not fit the normal anatomy of a patient eye and is thus inadequate based on human factors. Simply put, a user's facial features will occupy the same space as the enlarged patient interface necessary to accommodate a visualization beam splitter for high NA laser systems.

FIG. 17 illustrates a patient interface according to an embodiment of the present invention. To overcome the issues described above, a rotatable protruding portion 192 of the patient interface 190 is rotatable about an axis 191 and provided on the temporal side of the patient head. To fit both left and right eyes of a patient, the visualization optics (including the beam splitting optics, the patient interface 190, the imaging optics, and the CCD) are rotated 180 degrees in accordance with treating left and right eyes, respectively. In this manner, the larger visualization beam splitter elements are better positioned to avoid conflict with a user's face.

Figure 18A:
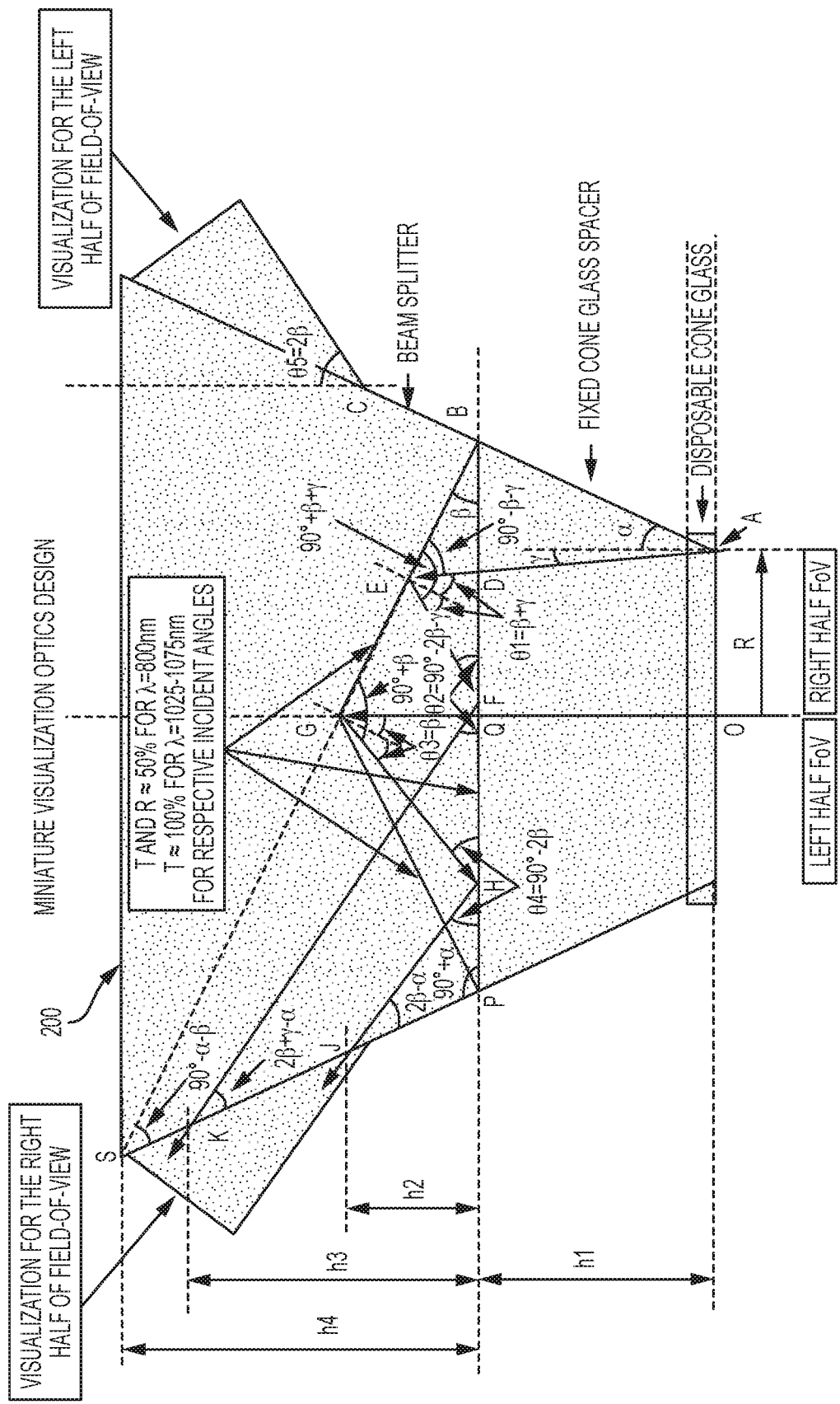
FIG. 18A-18B illustrate beam splitter optics according to an embodiment of the present invention.
Figure 18B:
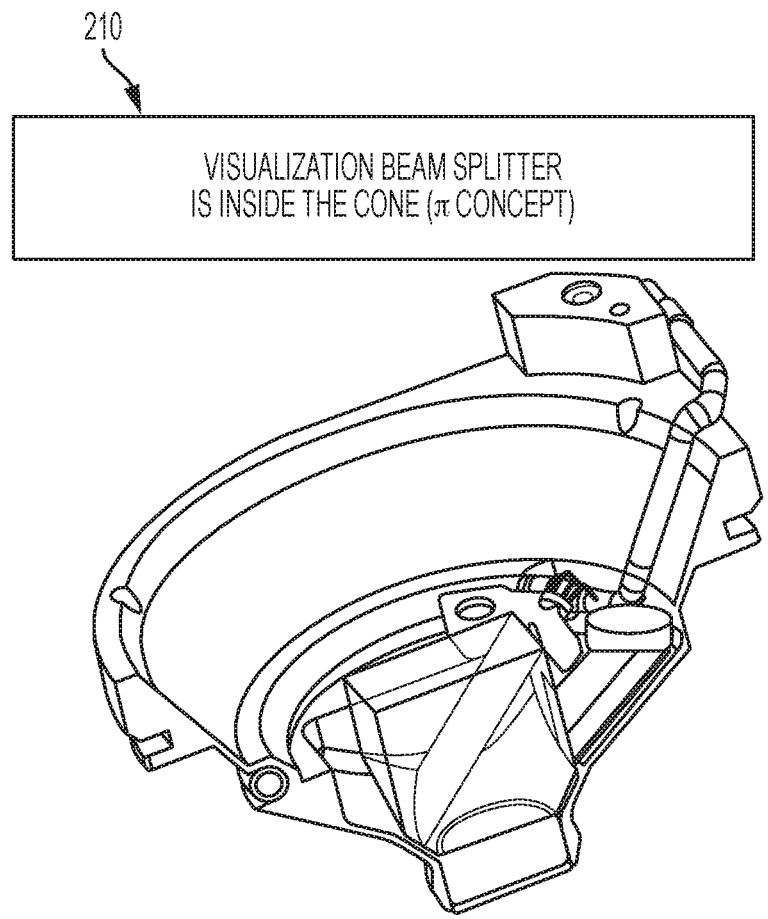

FIGS. 18A-18B illustrate beam splitting optics according to an embodiment of the present invention. A patient interface 200 is provided including two beam-splitting surfaces, BG and GP. These two surfaces divide the full field of view into left half and right half, and form two separate visualization channels. As a result, this reduction in the size of the channels allows the channels to fit into the cone of the patient interface 200 such that no rotation of the visualization beam splitter is needed when treating left and right eyes. Furthermore, the channels support high NA (NA=0.6) surgical beams. FIG. 18B illustrates a cross-sectional perspective view of the visualization beam splitter in the cone.

An interface for coupling a patient's eye to an ophthalmic surgical laser system includes a lens cone defining a first plane surface coupled with a delivery tip of the ophthalmic laser system. The lens cone includes an apex ring coupled to the first plane surface. The apex ring includes a distal end including a first receptacle configured to receive an attachment ring, the attachment ring configured to overlay an anterior surface of the patient's eye. The first receptacle and the attachment ring may be disposable. A central cavity is provided to receive the lens cone. A contact lens may applanate the anterior surface of the patient's eye.

One or more beam-splitter optics are provided to allow a pulsed laser beam to pass through the interface to a focal point of the target in the patient's eye. The beam-splitter optics may include one or more multi-facet beam-splitter optics and a side-imaging optical channel that is configured to rotate to a temporal side of the patient's eye. Alternatively, the beam-splitter optics may include dual imaging channels. The beam-splitter optics may be provided to manipulate non-centric imaging rays at a full optical cone angle equal to or greater than fifteen degrees.

FIG. 19 illustrates a table of visualization parameters according to an embodiment of the present invention. The specific numerical values for the half cone angle (α), the beam splitting surface angle (β), and the edge ray incident angle (γ), and the geometry dimensions of the visualization beam splitter are given in table 220.

Figure 20:
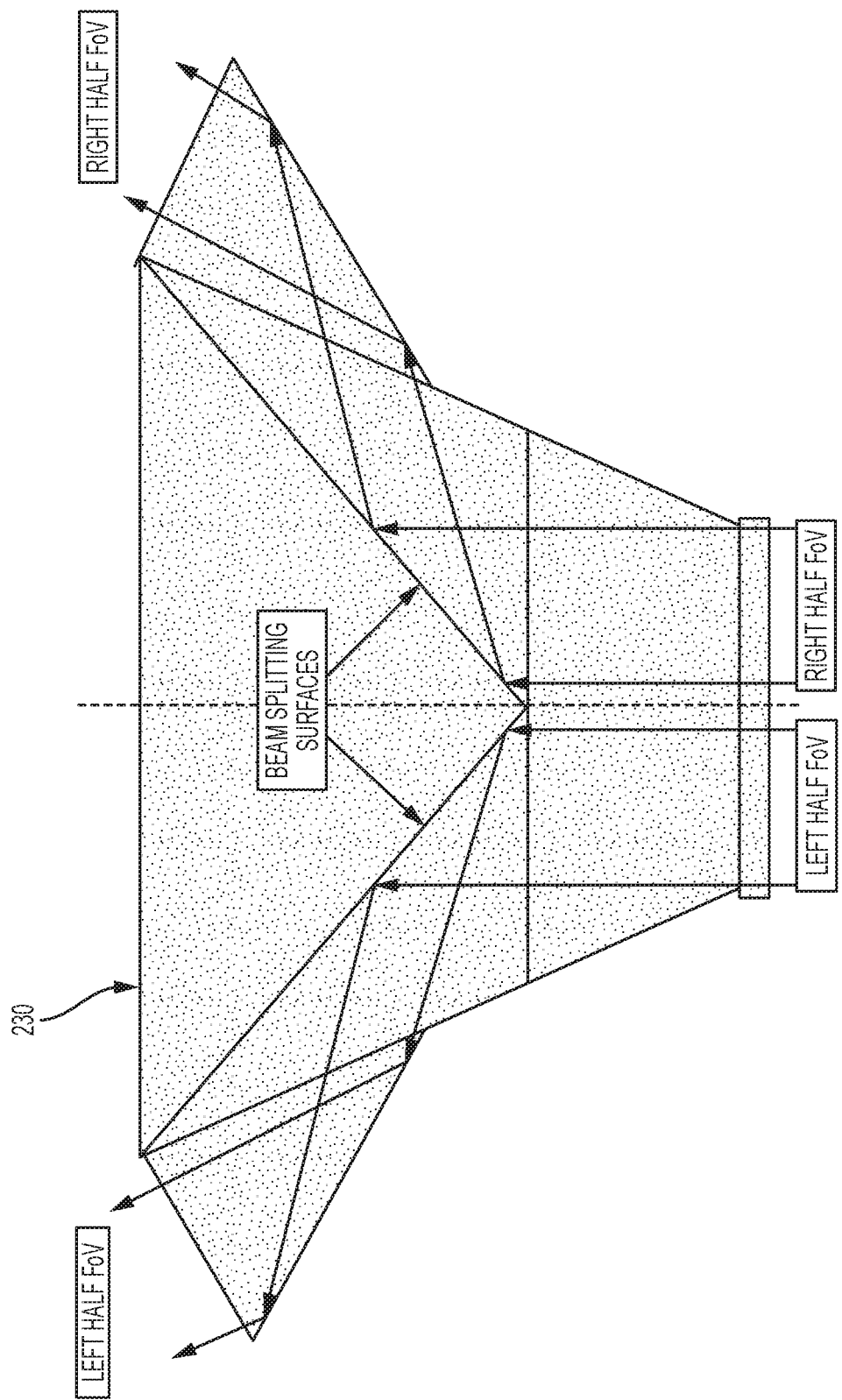
FIG. 20 illustrates beam splitter optics according to another embodiment of the present invention.

FIG. 20 illustrates beam splitting optics according to another embodiment of the present invention. The patient interface 230 in FIG. 20 divides the full field of view into two halves, images the two halves into two different optical channels, and processes to combine the two half-images together to reconstruct the full field of view. In this manner, the entire visualization beam splitting optics can be placed inside the cone of a compact patient interface 230.

This approach of dividing the full field of view into several smaller fields, and then combining the images of the smaller results to reconstruct the original large field of view may also be applied to measurement such as an optical channel for Optical Coherence Tomography, for ophthalmology surgical lasers including but not limited to femtosecond laser workstations.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
a laser delivery system configured to deliver a pulsed laser beam at a focal point of a target in a patient's eye, the pulsed laser beam having a pulse repetition rate in the range between 5 MHz and 25 MHz;
a resonant optical scanner, the scanner oscillating at a frequency between 200 Hz and 21000 Hz and configured to scan the pulsed laser beam to form a scan line which extends linearly in a lateral orientation;
a scan-line rotator disposed after the resonant optical scanner and configured to receive the scan line formed by the resonant optical scanner and rotate the lateral orientation of the scan line;
an xy-scan device configured to move the rotated scan line of the pulsed laser beam in two lateral directions;
a z-scan device configured to modify a depth of focus of the pulsed laser beam; and
a controller operably coupled with the laser delivery system, the resonant optical scanner, the scan-line rotator, the xy-scan device and the z-scan device, the controller configured to direct the laser delivery system to output the pulsed laser beam in a desired pattern at the focal point of the target in the eye so as to modify the target.

2. The ophthalmic surgical laser system of claim 1, wherein the laser delivery system comprises a diode-pumped fiber laser.

3. The ophthalmic surgical laser system of claim 2, wherein the diode-pumped fiber laser comprises a mode-locked fiber oscillator-based laser.

4. The ophthalmic surgical laser system of claim 3, wherein the mode-locked fiber oscillator-based laser comprises a single-mode, double-clad fiber oscillator.

5. The ophthalmic surgical laser system of claim 2, wherein the laser delivery system further comprises a fiber laser amplifier.

6. The ophthalmic surgical laser system of claim 2, wherein the mode-locked fiber oscillator laser further comprises all positive dispersion elements.

7. The ophthalmic surgical laser system of claim 1, wherein the laser delivery system delivers the pulsed laser beam at the focal point of the target in a patient's eye in a raster pattern.

8. The ophthalmic surgical laser system of claim 1, wherein the laser delivery system is configured to produce the pulsed laser beam having a pulse duration between the range of 10 femtoseconds and 10 picoseconds.

9. The ophthalmic surgical laser system of claim 1, wherein the laser delivery system is configured to produce the pulsed laser beam having a pulse energy between the range of 1 nJ and 5 µJ.

10. The ophthalmic surgical laser system of claim 1, wherein the laser delivery system is configured to produce the pulsed laser beam having a wavelength between the range of 1020 nm and 1065 nm.

11. The ophthalmic surgical laser system of claim 1, wherein the laser delivery system further comprises a close-loop control mechanism.

12. The ophthalmic surgical laser system of claim 1, wherein the focal point of the target in the patient's eye includes one or more of a cornea, stroma, capsular bag, crystalline lens, and zonule.

13. The ophthalmic surgical laser system of claim 1, wherein the xy scan device is a movable xy scanning stage having a final focusing objective mounted thereon.

14. The ophthalmic surgical laser system of claim 13, wherein the movable xy-scanning stage comprises a recoil-less stage configured to reduce or eliminate mechanical vibration.

15. The ophthalmic surgical laser system of claim 13, wherein the xy-scanning stage is configured to move the pulsed laser beam in a lateral direction such that the laser beam covers the entire surgical field of the patient's eye.

16. The ophthalmic surgical laser system of claim 1, wherein the pulsed laser beam modifies the target in the patient's eye to produce corneal tissue modification.

17. The ophthalmic surgical laser system of claim 16, wherein the corneal tissue modification comprises corneal cross-linking.

18. The ophthalmic surgical laser system of claim 1, wherein the pulsed laser beam modifies the target in the patient's eye to produce a desired incision.

19. The ophthalmic surgical laser system of claim 18, wherein the desired incision includes one or more of an xy lamellar dissection, a spiral lamellar dissection, a vertical side-cut, an angled side cut, a plano-vertical side cut, an intrastromal incision, a lenticular incision, and any three-dimensional dissection.

20. The ophthalmic surgical laser system of claim 1 further comprising: an imaging video camera.

21. The ophthalmic surgical laser system of claim 1, wherein the z-scan device is a voice coil scan device.

22. The ophthalmic surgical laser system of claim 1 further comprising: a beam expander.

23. The ophthalmic surgical laser system of claim 1, wherein the laser delivery system delivers the pulsed laser beam to the focal point of the target in the patient's eye while the patient is seated in an upright position.

24. The ophthalmic surgical laser system of claim 1, wherein the laser delivery system delivers the pulsed laser beam to the focal point of the target in the patient's eye while the patient is in a reclining position.

25. The ophthalmic surgical laser system of claim 1 further comprising: a patient interface for coupling the patient's eye to the ophthalmic surgical laser system.

26. The ophthalmic surgical laser system of claim 25 further comprising: an auto-z module, the auto-z module configured to measure a distal end of a lens cone of the patient interface coupled to the patient's eye and to provide a depth reference forthe z-scan device of the ophthalmic laser system.

27. The ophthalmic surgical laser system of claim 1, wherein the scan-line rotator is a rotatable prism.

28. The ophthalmic surgical laser system of claim 27, wherein the scan-line rotator is a rotatable Dove prism or a rotatable Pechan prism.

* * * * *